(12) United States Patent
Chinta et al.

(10) Patent No.: US 11,932,537 B2
(45) Date of Patent: Mar. 19, 2024

(54) INTEGRATED INDIRECT HEAT TRANSFER PROCESS FOR THE PRODUCTION OF SYNGAS AND OLEFINS BY CATALYTIC PARTIAL OXIDATION AND CRACKING

(71) Applicant: ENI S.p.A., Rome (IT)

(72) Inventors: Sivadinarayana Chinta, Sugar Land, TX (US); Miasser Al-Ghamdi, Thuwal (SA); Atul Pant, Bengaluru (IN); Ravichander Narayanaswamy, Bengaluru (IN)

(73) Assignee: ENI S.P.A., Rome (IT)

(*) Notice: Subject to any disclaimer, the term of this patent is extended or adjusted under 35 U.S.C. 154(b) by 176 days.

(21) Appl. No.: 17/433,811

(22) PCT Filed: Feb. 26, 2020

(86) PCT No.: PCT/US2020/019935
§ 371 (c)(1),
(2) Date: Aug. 25, 2021

(87) PCT Pub. No.: WO2020/176646
PCT Pub. Date: Sep. 3, 2020

(65) Prior Publication Data
US 2022/0144632 A1 May 12, 2022

Related U.S. Application Data

(60) Provisional application No. 62/810,629, filed on Feb. 26, 2019.

(51) Int. Cl.
*C01B 3/38* (2006.01)
*B01J 19/00* (2006.01)
(Continued)

(52) U.S. Cl.
CPC .......... *C01B 3/382* (2013.01); *B01J 19/0013* (2013.01); *B01J 19/245* (2013.01); *C07C 4/04* (2013.01);
(Continued)

(58) Field of Classification Search
CPC ............ C01B 3/382; C01B 2203/0244; C01B 2203/0261; C01B 2203/0833;
(Continued)

(56) References Cited

U.S. PATENT DOCUMENTS

2007/0000176 A1 1/2007 Liu et al.
2007/0144940 A1 6/2007 Hershkowitz et al.
(Continued)

FOREIGN PATENT DOCUMENTS

WO 2018170263 A1 9/2018
WO 2018234971 A1 12/2018

OTHER PUBLICATIONS

International Search Report dated Jun. 30, 2020 re: Application No. PCT/US2020/019935, pp. 1-4, citing: US 2007/0000176 A1, WO 2018/234971 A1, US 2007/0144940 A1, US 2012/0028794 A1 and WO 2018/170263 A1.
(Continued)

*Primary Examiner* — Jafar F Parsa
(74) *Attorney, Agent, or Firm* — CANTOR COLBURN LLP

(57) ABSTRACT

A process for producing syngas and olefins includes the steps of feeding a catalytic partial oxidation (CPO) reactant mixture having oxygen, first hydrocarbons, and optionally steam to a CPO reaction zone having a CPO catalyst such that at least a portion of the CPO reactant mixture reacts, via an exothermic CPO reaction, to produce syngas having hydrogen ($H_2$), carbon monoxide (CO), carbon dioxide ($CO_2$), water, and unreacted first hydrocarbons. The syngas
(Continued)

is characterized by a molar ratio M defined as $(H_2-CO_2)/(CO+CO_2)$. The method further includes feeding a cracking zone feed having second hydrocarbons to a cracking zone such that at least a portion of the second hydrocarbons undergoes an endothermic cracking reaction to produce a cracking zone product stream having olefins, hydrogen, and unreacted second hydrocarbons; and cooling the CPO reaction zone by heating the cracking zone while cooling the CPO reaction zone via heat transfer between the CPO reaction zone and the cracking zone.

16 Claims, 3 Drawing Sheets

(51) Int. Cl.
    *B01J 19/24*     (2006.01)
    *C07C 4/04*     (2006.01)
    *C07C 29/151*     (2006.01)

(52) U.S. Cl.
    CPC ... *C07C 29/1518* (2013.01); *B01J 2219/0004* (2013.01); *B01J 2219/00074* (2013.01); *C01B 2203/0244* (2013.01); *C01B 2203/0261* (2013.01); *C01B 2203/0833* (2013.01); *C01B 2203/1247* (2013.01); *C01B 2203/148* (2013.01)

(58) Field of Classification Search
    CPC ...... C01B 2203/1247; C01B 2203/148; C07C 29/1518; C07C 31/04; C07C 11/04; C07C 5/333; C07C 4/025; C07C 5/327; C10G 2400/20; C10G 9/40
    See application file for complete search history.

(56)     References Cited

U.S. PATENT DOCUMENTS

2012/0028794 A1     2/2012     Lam et al.
2017/0137355 A1     5/2017     Sarsani et al.

OTHER PUBLICATIONS

Written Opinion dated Jun. 30, 2020 re: Application No. PCT/US2020/019935, pp. 1-8, citing: US 2007/0000176 A1, WO 2018/234971 A1 and US 2007/0144940 A1.
European Search Report for European Application No. 20763005.4, dated Nov. 8, 2022, 7 pages.

INTEGRATED INDIRECT HEAT TRANSFER PROCESS FOR THE PRODUCTION OF SYNGAS AND OLEFINS BY CATALYTIC PARTIAL OXIDATION AND CRACKING

TECHNICAL FIELD

The present disclosure relates to methods of producing methanol, more specifically methods of producing methanol from syngas produced by catalytic partial oxidation (CPO) of hydrocarbons, such as methane, integrated with cracking such that at least a portion of the heat needed for the cracking is provided by the CPO.

BACKGROUND

Synthesis gas (syngas) is a mixture comprising carbon monoxide (CO) and hydrogen ($H_2$), as well as small amounts of carbon dioxide ($CO_2$), water ($H_2O$), and unreacted methane ($CH_4$). Syngas is generally used as an intermediate in the production of methanol and ammonia, as well as an intermediate in creating synthetic petroleum to use as a lubricant or fuel. Syngas is produced conventionally by steam reforming of natural gas (steam methane reforming or SMR), although other hydrocarbon sources can be used for syngas production, such as refinery off-gases, naphtha feedstocks, heavy hydrocarbons, coal, biomass, etc. SMR is an endothermic process and requires significant energy input to drive the reaction forward. Conventional endothermic technologies such as SMR produce syngas with a hydrogen content greater than the required content for methanol synthesis. Generally, SMR produces syngas with an M ratio ranging from 2.6 to 2.98, wherein the M ratio is a molar ratio defined as $(H_2-CO_2)/(CO+CO_2)$.

In an autothermal reforming (ATR) process, a portion of the natural gas is burned as fuel to drive the conversion of natural gas to syngas resulting in relatively low hydrogen and high $CO_2$ concentrations. Conventional methanol production plants utilize a combined reforming (CR) technology that pairs SMR with autothermal reforming (ATR) to reduce the amount of hydrogen present in syngas. ATR produces a syngas with a hydrogen content lower than the required content for methanol synthesis. Generally, ATR produces syngas with an M ratio ranging from 1.7 to 1.84. In the CR technology, the natural gas feed volumetric flowrate to the SMR and the ATR can be adjusted to achieve an overall syngas M ratio of 2.0 to 2.06. Further, CR syngas has a hydrogen content greater than the required content for methanol synthesis. Furthermore, SMR is a highly endothermic process, and the endothermicity of the SMR technology requires burning fuel to drive the syngas synthesis. Consequently, the SMR technology reduces the energy efficiency of the methanol synthesis process.

Syngas can also be produced (non-commercially) by catalytic partial oxidation (CPO or CPOx) of natural gas. CPO processes employ partial oxidation of hydrocarbon feeds to syngas comprising CO and $H_2$. The CPO process is exothermic, thus eliminating the need for external heat supply. However, the composition of the produced syngas is not suitable for methanol synthesis, for example, owing to a reduced hydrogen content. Further, maintaining a desired catalyst activity and productivity can be challenging in a CPO process, owing to elevated or run-away CPO temperatures leading to catalyst deactivation. The CPO reaction is exothermic, and can lead to a high temperature increase in a CPO catalyst bed, which can in turn lead to catalyst deactivation. Thus, there is an ongoing need for the development of syngas production via CPO processes that manage the reaction temperature, as well as produce a syngas that is suitable for a methanol production process.

BRIEF DESCRIPTION OF THE DRAWINGS

For a detailed description of the preferred embodiments of the disclosed methods, reference will now be made to the accompanying drawing in which.

DETAILED DESCRIPTION

Figure 1:
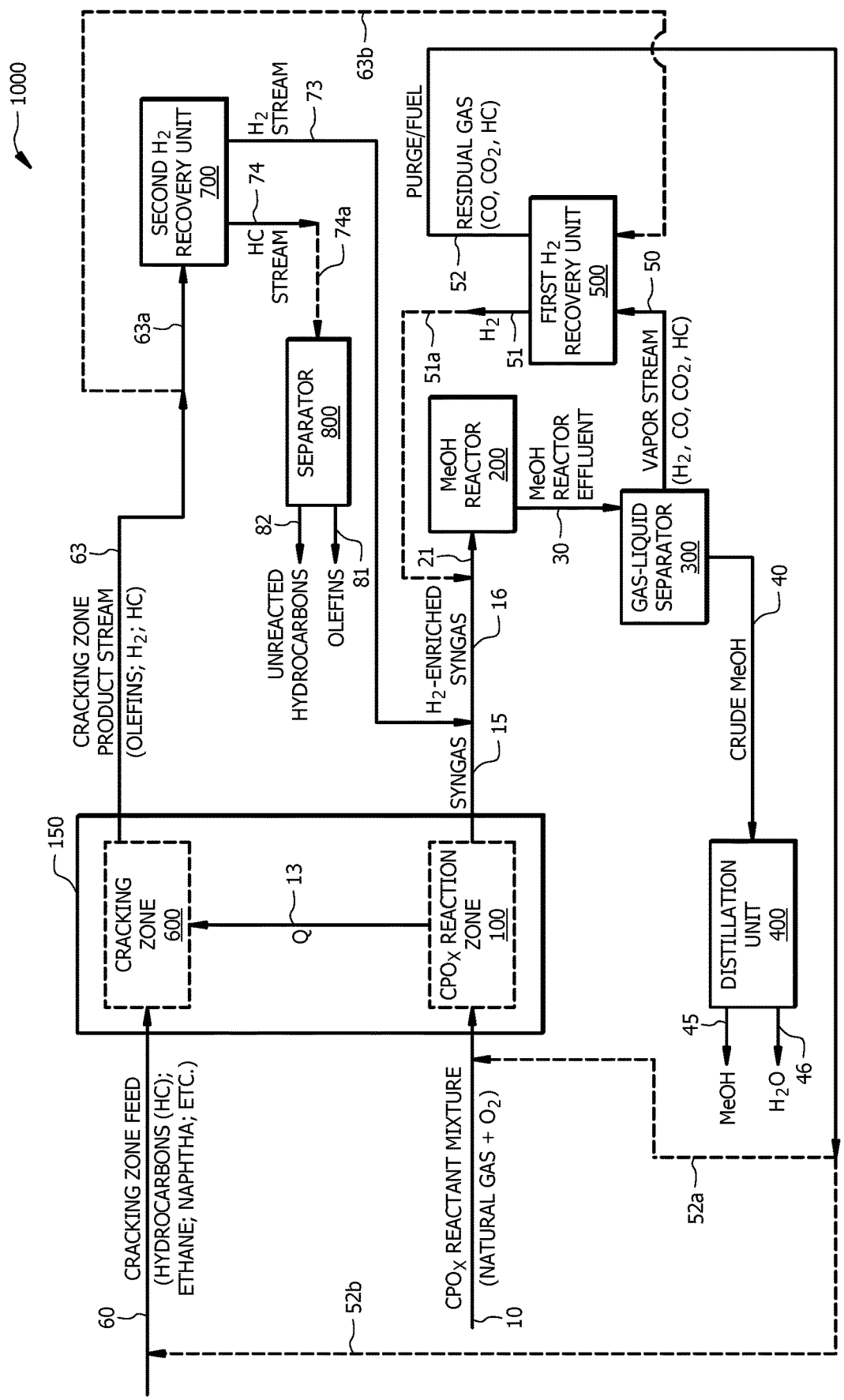
FIG. 1 displays a schematic of a system for a methanol production process.

Disclosed herein are processes for producing syngas and olefins comprising: (a) feeding a catalytic partial oxidation (CPO) reactant mixture to a CPO reaction zone; wherein the CPO reactant mixture comprises oxygen, first hydrocarbons, and optionally steam; wherein at least a portion of the CPO reactant mixture reacts, via an exothermic CPO reaction, in the CPO reaction zone to produce syngas; wherein the CPO reaction zone comprises a CPO catalyst; wherein the syngas comprises hydrogen ($H_2$), carbon monoxide (CO), carbon dioxide ($CO_2$), water, and unreacted first hydrocarbons, and wherein the syngas is characterized by an M ratio of the syngas, wherein the M ratio is a molar ratio defined as $(H_2-CO_2)/(CO+CO_2)$; (b) feeding a cracking zone feed to a cracking zone, wherein the cracking zone feed comprises second hydrocarbons; wherein at least a portion of the second hydrocarbons undergoes an endothermic cracking reaction in the cracking zone to produce a cracking zone product stream; wherein the first hydrocarbons and the second hydrocarbons are the same or different; wherein the cracking zone product stream comprises olefins, $H_2$, and unreacted second hydrocarbons; and (c) cooling the CPO reaction zone; wherein cooling the CPO reaction zone comprises heating the cracking zone while cooling the CPO reaction zone by heat transfer (e.g., indirect heat transfer) between the CPO reaction zone and the cracking zone.

In some embodiments, the method can further comprise: (1) separating at least a portion of the cracking zone product stream into a hydrogen stream and a hydrocarbons stream, wherein the hydrocarbons stream comprises olefins and unreacted hydrocarbons; (2) optionally contacting at least a portion of the hydrogen stream with at least a portion of the syngas to produce a hydrogen-enriched syngas, wherein the hydrogen-enriched syngas is characterized by an M ratio greater than the M ratio of the syngas, and wherein the M ratio of the hydrogen-enriched syngas is equal to or greater than about 1.7; (3) optionally introducing at least a portion of the syngas and/or at least a portion of the hydrogen-enriched syngas to a methanol reactor to produce methanol; (4) optionally separating at least a portion of the hydrocarbons stream into an olefins stream and an unreacted hydrocarbons stream, wherein the olefins stream comprises at least a portion of the olefins in the hydrocarbons stream, and wherein the unreacted hydrocarbons stream comprises at least a portion of the unreacted hydrocarbons in the hydrocarbons stream; and (5) optionally recycling at least a portion of the hydrocarbons stream and/or at least a portion of the unreacted hydrocarbons stream to the cracking zone in step (b) and/or to the CPO reaction zone in step (a). The first hydrocarbons and/or the second hydrocarbons can comprise methane, ethane, propane, butanes, naptha, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, or combinations thereof. In embodiments, the second hydrocarbons comprise $C_2H_6$, propane, butane, naphtha, optionally $CH_4$, or combinations thereof; and the olefins comprise ethylene.

In order to adjust the $H_2$/CO molar ratios of syngas to values greater than about 1.7-1.9, the processes disclosed herein illustrate methods for enhancing the $H_2$/CO molar ratio and/or decreasing the hydrocarbon concentration in syngas (e.g., decrease methane slip). In an embodiment, a hydrogen stream that has a hydrogen-rich content can be blended with a CPO reaction zone effluent in any suitable proportions to provide for a hydrogen-enriched syngas having a $H_2$/CO molar ratio of greater than about 1.7, 1.8, 1.9, or 2.0. Run-away temperatures in the CPO reaction zone can be avoided by utilizing heat from the exothermic CPO reaction in the CPO reaction zone to provide heat for endothermic cracking of the cracking zone feed in the cracking zone.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an embodiment," "another embodiment," "other embodiments," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art. Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group. As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof. As used herein, the term "$C_{x+}$ hydrocarbons" refers to any hydrocarbon having equal to or greater than x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

Referring to FIG. 1, a methanol production system 1000 is disclosed. The methanol production system 1000 generally comprises a catalytic partial oxidation (CPO or CPOx) reaction zone 100; a methanol reactor 200; a gas-liquid separator 300; a distillation unit 400; a first hydrogen ($H_2$) recovery unit 500; a cracking zone 600; and a separation unit comprising second $H_2$ recovery unit 700 and separator 800. Common reference numerals refer to common components present in one or more of the Figures, and the description of a particular component is generally applicable across respective Figures wherein the component is present, except as otherwise indicated herein.

In an embodiment, a process as disclosed herein can comprise a step of reacting, via a CPO reaction, a CPO reactant mixture 10 in the CPO reaction zone 100 to produce a CPO reaction zone effluent comprising syngas 15; wherein the CPO reactant mixture 10 comprises oxygen ($O_2$), hydrocarbons (e.g., first hydrocarbons) and optionally steam; wherein the CPO reaction zone 100 comprises a CPO catalyst; and wherein the CPO reaction zone effluent (e.g., syngas 15) comprises hydrogen ($H_2$), carbon monoxide (CO), carbon dioxide ($CO_2$), water, and unreacted first hydrocarbons, and wherein the syngas is characterized by an M ratio of the syngas, wherein the M ratio is a molar ratio defined as ($H_2$−$CO_2$)/(CO+$CO_2$). As will be appreciated by one of skill in the art, and with the help of this disclosure, depending on the composition of the CPO reactant mixture 10, the composition of the resulting CPO reaction zone effluent (e.g., syngas 15) recovered from the CPO reaction zone 100 can vary.

Generally, the CPO reaction is based on partial combustion of fuels, such as various hydrocarbons, and in the case of methane, CPO can be represented by equation (1):

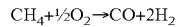
$$CH_4 + \tfrac{1}{2}O_2 \rightarrow CO + 2H_2 \qquad (1)$$

Without wishing to be limited by theory, side reactions can take place along with the CPO reaction depicted in equation (1); and such side reactions can produce carbon dioxide ($CO_2$) and water ($H_2O$), for example via hydrocarbon combustion, which is an exothermic reaction. As will be appreciated by one of skill in the art, and with the help of this disclosure, and without wishing to be limited by theory, the CPO reaction as represented by equation (1) can yield a syngas with a hydrogen to CO ($H_2$/CO) molar ratio having the theoretical stoichiometric limit of 2.0. Without wishing to be limited by theory, the theoretical stoichiometric limit of 2.0 for the $H_2$/CO molar ratio means that the CPO reaction as represented by equation (1) yields 2 moles of $H_2$ for every 1 mole of CO, i.e., $H_2$/CO molar ratio of (2 moles $H_2$/1 mole CO)=2. As will be appreciated by one of skill in the art, and with the help of this disclosure, the theoretical stoichiometric limit of 2.0 for the $H_2$/CO molar ratio in a CPO reaction cannot be achieved practically because reactants (e.g., hydrocarbons, $O_2$) as well as products (e.g., $H_2$, CO) undergo side reactions at the conditions used for the CPO reaction. As will be appreciated by one of skill in the art, and with the help of this disclosure, and without wishing to be limited by theory, in the presence of $O_2$, CO and $H_2$ can be oxidized to $CO_2$ and $H_2O$, respectively. The relative amounts (e.g., composition) of CO, $H_2$, $CO_2$ and $H_2O$ can be further altered by the equilibrium of the water-gas shift (WGS) reaction, which will be discussed in more detail later herein. The side reactions that can take place in the CPO reaction zone 100 can have a direct impact on the M ratio of the produced syngas 15, wherein the M ratio is a molar ratio defined as $(H_2-CO_2)/(CO+CO_2)$. In the absence of any side reaction (theoretically), the CPO reaction as represented by equation (1) results in a syngas with an M ratio of 2.0. However, the presence of side reactions (practically) reduces $H_2$ and increases $CO_2$, thereby resulting in a syngas with an M ratio below 2.0.

Further, without wishing to be limited by theory, the CPO reaction as depicted in equation (1) is an exothermic heterogeneous catalytic reaction (i.e., a mildly exothermic reaction) and it occurs in a single reactor unit, such as the CPO reaction zone 100 (as opposed to more than one reactor unit as is the case in conventional processes for syngas production, such as steam methane reforming (SMR)-autothermal reforming (ATR) combinations). While it is possible to conduct partial oxidation of hydrocarbons as a homogeneous reaction, in the absence of a catalyst, homogeneous partial oxidation of hydrocarbons process entails excessive temperatures, long residence times, as well as excessive coke formation, which strongly reduce the controllability of the partial oxidation reaction, and may not produce syngas of the desired quality in a single reaction zone. Furthermore, without wishing to be limited by theory, the CPO reaction is fairly resistant to chemical poisoning, and as such it allows for the use of a wide variety of hydrocarbon feedstocks, including some sulfur containing hydrocarbon feedstocks; which, in some cases, can enhance catalyst life-time and productivity. By contrast, conventional ATR processes have more restrictive feed requirements, for example in terms of content of impurities in the feed (e.g., feed to ATR is desulfurized), as well as hydrocarbon composition (e.g., ATR primarily uses a $CH_4$-rich feed).

In an embodiment, the hydrocarbons (e.g., first hydrocarbons) suitable for use in a CPO reaction as disclosed herein can include methane ($CH_4$), ethane, propane, butanes, naphtha, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, and the like, or combinations thereof. The hydrocarbons (e.g., first hydrocarbons) can include any suitable hydrocarbons source, and can contain $C_1$-$C_6$ hydrocarbons, as well as some heavier hydrocarbons.

In an embodiment, CPO reactant mixture 10 can comprise natural gas. Generally, natural gas is composed primarily of methane, but can also contain ethane, propane and heavier hydrocarbons (e.g., iso-butane, n-butane, iso-pentane, n-pentane, hexanes, etc.), as well as very small quantities of nitrogen ($N_2$), $O_2$, $CO_2$, sulfur compounds, and/or water. The natural gas can be provided from a variety of sources including, but not limited to, gas fields, oil fields, coal fields, fracking of shale fields, biomass, landfill gas, and the like, or combinations thereof. The CPO reactant mixture 10 can comprise $CH_4$ and $O_2$.

The natural gas can comprise any suitable amount of methane. In some embodiments, the natural gas can comprise biogas. For example, the natural gas can comprise from about 45 mol % to about 80 mol % methane, from about 20 mol % to about 55 mol % $CO_2$, and less than about 15 mol % $N_2$.

In an embodiment, natural gas can comprise $CH_4$ in an amount of equal to or greater than about 45 mol %, about 50 mol %, about 55 mol %, about 60 mol %, about 65 mol %, about 70 mol %, about 75 mol %, about 80 mol %, about 82 mol %, about 84 mol %, about 86 mol %, about 88 mol %, about 90 mol %, about 91 mol %, about 92 mol %, about 93 mol %, about 94 mol %, about 95 mol %, about 96 mol %, about 97 mol %, about 98 mol %, or about 99 mol %.

In some embodiments, the hydrocarbons (e.g., first hydrocarbons) suitable for use in a CPO reaction as disclosed herein can comprise $C_1$-$C_6$ hydrocarbons, $N_2$ (e.g., from about 0.1 mol % to about 15 mol %, about 0.5 mol % to about 11 mol %, about 1 mol % to about 7.5 mol %, or about 1.3 mol % to about 5.5 mol %), and $CO_2$ (e.g., from about 0.1 mol % to about 2 mol %, about 0.2 mol % to about 1 mol %, or about 0.3 mol % to about 0.6 mol %). For example, the hydrocarbons (e.g., first hydrocarbons) suitable for use in a CPO reaction as disclosed herein can comprise $C_1$ hydrocarbon (about 89 mol % to about 92 mol %); $C_2$ hydrocarbons (about 2.5 mol % to about 4 mol %); $C_3$ hydrocarbons (about 0.5 mol % to about 1.4 mol %); $C_4$ hydrocarbons (about 0.5 mol % to about 0.2 mol %); $C_5$ hydrocarbons (about 0.06 mol %); and $C_6$ hydrocarbons (about 0.02 mol %); and optionally $N_2$ (about 0.1 mol % to about 15 mol %), $CO_2$ (about 0.1 mol % to about 2 mol %), or both $N_2$ (about 0.1 mol % to about 15 mol %) and $CO_2$ (about 0.1 mol % to about 2 mol %).

In an aspect, the CPO reactant mixture 10 can comprise any suitable amount of $CO_2$. In an aspect, the CPO reactant mixture 10 can comprise an amount of $CO_2$ effective to provide for a syngas 15 with a desired composition (e.g., a syngas with a desired $H_2$/CO molar ratio; a syngas with a desired M ratio; a syngas with a desired $CO_2$ content; etc.). In some aspects, the CPO reactant mixture 10 can comprise $CO_2$ in an amount of from about 0.01 mol % to about 5 mol %, alternatively from about 0.1 mol % to about 2 mol %, alternatively from about 0.2 mol % to about 1 mol %, or alternatively from about 0.3 mol % to about 0.6 mol %. In other aspects, the CPO reactant mixture 10 can comprise $CO_2$ in an amount of equal to or greater than about 5 mol %, about 10 mol %, or about 15 mol %.

In some aspects, the CPO reactant mixture 10 can comprise any suitable amount of hydrocarbons. The hydrocarbons (e.g., first hydrocarbons) suitable for use in a CPO reaction as disclosed herein can comprise $C_1$-$C_6$ hydrocarbons (optionally including some amount of $C_7$ hydrocarbons), optionally $N_2$ (e.g., from 0 wt. % to about 10 wt. %, alternatively from about 0.1 wt. % to about 5 wt. %, alternatively from about 0.2 wt. % to about 2.5 wt. %, or alternatively from about 0.25 wt. % to about 1 wt. %, based on the total weight of the hydrocarbons), and $CO_2$ (e.g., from about 0.01 wt. % to about 5 wt. %, alternatively from about 0.02 wt. % to about 1 wt. %, or alternatively from about 0.025 wt. % to about 0.5 wt. %, based on the total weight of the hydrocarbons). For example, the hydrocarbons (e.g., first hydrocarbons) suitable for use in a CPO reaction as disclosed herein can comprise $C_1$ hydrocarbon (about 0.01 wt. % to about 10 wt. %, alternatively about 0.05 wt. % to about 5 wt. %, or alternatively about 0.1 wt. % to about 1 wt. %, based on the total weight of the hydrocarbons); $C_2$ hydrocarbons (about 15 wt. % to about 75 wt. %, alternatively about 20 wt. % to about 60 wt. %, or alternatively about 25 wt. % to about 50 wt. %, based on the total weight of the hydrocarbons); $C_3$ hydrocarbons (about 15 wt. % to about 50 wt. %, alternatively about 20 wt. % to about 40 wt. %, or alternatively about 25 wt. % to about 35 wt. %, based on the total weight of the hydrocarbons); $C_4$ hydrocarbons, such as normal-$C_4$ and/or iso-$C_4$ (about 5 wt. % to about 40 wt. %, alternatively about 10 wt. % to about 30 wt. %, or alternatively about 15 wt. % to about 25 wt. %, based on the total weight of the hydrocarbons); $C_5$ hydrocarbons, such as normal-$C_5$ and/or iso-$C_5$ (about 1 wt. % to about 20 wt. %, alternatively about 2.5 wt. % to about 15 wt. %, or alternatively about 5 wt. % to about 10 wt. %, based on the total weight of the hydrocarbons); and $C_6$ hydrocarbons, including $C_6$ hydrocarbons (about 1 wt. % to about 15 wt. %, alternatively about 1.5 wt. % to about 10 wt. %, or alternatively about 2.5 wt. % to about 7.5 wt. %, based on the total weight of the hydrocarbons); and optionally $N_2$ (from 0 wt. % to about 10 wt. %, based on the total weight of the hydrocarbons) and/or $CO_2$ (from about 0.01 wt. % to about 5 wt. %, based on the total weight of the hydrocarbons).

The oxygen used in the CPO reactant mixture 10 can comprise 100% oxygen (substantially pure $O_2$), oxygen gas (which may be obtained via a membrane separation process), technical oxygen (which may contain some air), air, oxygen enriched air, oxygen-containing gaseous compounds (e.g., NO), oxygen-containing mixtures (e.g., $O_2/CO_2$, $O_2/H_2O$, $O_2/H_2O_2/H_2O$), oxy radical generators (e.g., $CH_3OH$, $CH_2O$), hydroxyl radical generators, and the like, or combinations thereof.

In an embodiment, the CPO reactant mixture 10 can be characterized by a carbon to oxygen (C/O) molar ratio of less than about 3:1, about 2.6:1, about 2.4:1, about 2.2:1, about 2:1, or about 1.9:1, alternatively equal to or greater than about 2:1, about 2.2:1, about 2.4:1, or about 2.6:1, alternatively from about 0.5:1 to about 3:1, alternatively from about 0.7:1 to about 2.5:1, alternatively from about 0.9:1 to about 2.2:1, alternatively from about 1:1 to about 2:1, alternatively from about 1.1:1 to about 1.9:1, alternatively from about 2:1 to about 3:1, alternatively from about 2.2:1 to about 3:1, alternatively from about 2.4:1 to about 3:1, or alternatively from about 2.6:1 to about 3:1, wherein the C/O molar ratio refers to the total moles of carbon (C) of hydrocarbons in the reactant mixture divided by the total moles of $O_2$ in the reactant mixture. For example, when the only source of carbon in the CPO reactant mixture 10 is $CH_4$, the $CH_4/O_2$ molar ratio is the same as the C/O molar ratio. As another example, when the CPO reactant mixture 10 contains other carbon sources besides $CH_4$, such as ethane ($C_2H_6$), propane ($C_3H_8$), butanes ($C_4H_{10}$), etc., the C/O molar ratio accounts for the moles of carbon in each compound (e.g., 2 moles of C in 1 mole of $C_2H_6$, 3 moles of C in 1 mole of $C_3H_8$, 4 moles of C in 1 mole of $C_4H_{10}$, etc.). As will be appreciated by one of skill in the art, and with the help of this disclosure, the C/O molar ratio in the CPO reactant mixture 10 can be adjusted along with other reactor process parameters (e.g., temperature, pressure, flow velocity, etc.) to provide for a syngas with a desired composition (e.g., a syngas with a desired $H_2/CO$ molar ratio; a syngas with a desired $CO_2$ content; etc.). The C/O molar ratio in the CPO reactant mixture 10 can be adjusted to provide for a decreased amount of unconverted hydrocarbons in the syngas 15. The C/O molar ratio in the CPO reactant mixture 10 can be adjusted based on the CPO effluent temperature in order to decrease (e.g., minimize) the unconverted hydrocarbons content of the syngas 15. As will be appreciated by one of skill in the art, and with the help of this disclosure, when the syngas is further used in a methanol production process, unconverted hydrocarbons present in the syngas can undesirably accumulate in a methanol reaction loop, thereby decreasing the efficiency of the methanol production process.

In an embodiment, a portion of the hydrocarbons (e.g., first hydrocarbons) in CPO reactant mixture 10 can undergo a thermal decomposition reaction to C and $H_2$, for example as represented by equation (2):

$$CH_4 \rightarrow C + 2H_2 \qquad (2)$$

The decomposition reaction of hydrocarbons, such as methane, is facilitated by elevated temperatures, and increases the $H_2$ content in the CPO reaction zone effluent (e.g., syngas 15). As will be appreciated by one of skill in the art, and with the help of this disclosure, and without wishing to be limited by theory, while the percentage of hydrocarbons in the CPO reactant mixture 10 that undergoes a decomposition reaction (e.g., a decomposition reaction as represented by equation (2)) increases with increasing the C/O molar ratio in the CPO reactant mixture 10, a portion of hydrocarbons can undergo a decomposition reaction to C and $H_2$ even at relatively low C/O molar ratios in the CPO reactant mixture 10 (e.g., a C/O molar ratio in the CPO reactant mixture 10 of less than about 2:1).

The CPO reaction is an exothermic reaction (e.g., heterogeneous catalytic reaction; exothermic heterogeneous catalytic reaction) that is generally conducted in the presence of a CPO catalyst comprising a catalytically active metal, i.e., a metal active for catalyzing the CPO reaction. The catalytically active metal can comprise a noble metal (e.g., Pt, Rh, Ir, Pd, Ru, Ag, and the like, or combinations thereof); a non-noble metal (e.g., Ni, Co, V, Mo, P, Fe, Cu, and the like, or combinations thereof); rare earth elements (e.g., La, Ce, Nd, Eu, and the like, or combinations thereof); oxides thereof; and the like; or combinations thereof. Generally, a noble metal is a metal that resists corrosion and oxidation in a water-containing environment. As will be appreciated by one of skill in the art, and with the help of this disclosure, the components of the CPO catalyst (e.g., metals such as noble metals, non-noble metals, rare earth elements) can be either phase segregated or combined within the same phase.

In an embodiment, the CPO catalysts suitable for use in the present disclosure can be supported catalysts and/or unsupported catalysts. In some embodiments, the supported catalysts can comprise a support, wherein the support can be catalytically active (e.g., the support can catalyze a CPO reaction). For example, the catalytically active support can comprise a metal gauze or wire mesh (e.g., Pt gauze or wire mesh); a catalytically active metal monolithic catalyst; etc. In other embodiments, the supported catalysts can comprise a support, wherein the support can be catalytically inactive (e.g., the support cannot catalyze a CPO reaction), such as $SiO_2$; silicon carbide (SiC); alumina; a catalytically inactive monolithic support; etc. In yet other embodiments, the supported catalysts can comprise a catalytically active support and a catalytically inactive support.

In some embodiments, a CPO catalyst can be wash coated onto a support, wherein the support can be catalytically active or inactive, and wherein the support can be a monolith, a foam, an irregular catalyst particle, etc. In some embodiments, the CPO catalyst can be a monolith, a foam, a powder, a particle, etc. Nonlimiting examples of CPO catalyst particle shapes suitable for use in the present disclosure include cylindrical, discoidal, spherical, tabular, ellipsoidal, equant, irregular, cubic, acicular, and the like, or combinations thereof. In some embodiments, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), zirconium oxide ($ZrO_2$), lanthanum (III) oxide ($La_2O_3$), yttrium (III) oxide ($Y_2O_3$), cerium (IV) oxide ($CeO_2$), zeolites, ZSM-5, perovskite oxides, hydrotalcite oxides, and the like, or combinations thereof.

CPO processes, CPO reactors, CPO catalysts, CPO reaction zones, and CPO catalyst bed configurations suitable for use in the present disclosure are described in more detail in U.S. Provisional Patent Application No. 62/522,910 filed Jun. 21, 2017 (International Application No. PCT/IB2018/054475 filed Jun. 18, 2018) and entitled "Improved Reactor Designs for Heterogeneous Catalytic Reactions;" and U.S. Provisional Patent Application No. 62/521,831 filed Jun. 19, 2017 (International Application No. PCT/IB2018/054470 filed Jun. 18, 2018) and entitled "An Improved Process for Syngas Production for Petrochemical Applications", each of which is incorporated by reference herein in its entirety.

In an embodiment, a CPO reactor suitable for use in the present disclosure (e.g., comprising CPO reaction zone 100) can comprise a tubular reactor, a continuous flow reactor, a fixed bed reactor, a fluidized bed reactor, a moving bed reactor, a riser type reactor, a bubbling bed reactor, a circulating bed reactor, an ebullated bed reactor, a rotary kiln reactor, and the like, or combinations thereof.

In some embodiments, the CPO reaction zone 100 can be characterized by at least one CPO operational parameter selected from the group consisting of a CPO reaction zone temperature (e.g., CPO catalyst bed temperature); CPO feed temperature (e.g., CPO reactant mixture temperature); target CPO effluent temperature; a CPO pressure (e.g., CPO reactor pressure, a CPO reaction zone pressure); a CPO contact time (e.g., CPO reaction zone contact time); a C/O molar ratio in the CPO reactant mixture; a steam to carbon (S/C) molar ratio in the CPO reactant mixture, wherein the S/C molar ratio refers to the total moles of water ($H_2O$) in the reactant mixture divided by the total moles of carbon (C) of hydrocarbons in the reactant mixture; and combinations thereof. For purposes of the disclosure herein, the CPO effluent temperature is the temperature of the syngas 15 measured at the point where the syngas exits the CPO reaction zone 100, e.g., a temperature of the syngas 15 measured at an exit of the CPO reaction zone 100. For purposes of the disclosure herein, the CPO effluent temperature (e.g., target CPO effluent temperature) is considered an operational parameter. As will be appreciated by one of skill in the art, and with the help of this disclosure, the choice of operational parameters for the CPO reaction zone 100 such as CPO feed temperature; CPO pressure; CPO contact time; C/O molar ratio in the CPO reactant mixture; S/C molar ratio in the CPO reactant mixture; a flow rate of a cracking zone feed 60, as described further hereinbelow; etc. determines the temperature of effluent syngas 15, as well as the composition of effluent syngas 15. Further, and as will be appreciated by one of skill in the art, and with the help of this disclosure, monitoring the CPO effluent temperature can provide feedback for changing other operational parameters (e.g., CPO feed temperature; CPO pressure; CPO contact time; C/O molar ratio in the CPO reactant mixture; S/C molar ratio in the CPO reactant mixture; flow rate of cracking zone feed 60; etc.), as necessary for the CPO effluent temperature to match the target CPO effluent temperature. Furthermore, and as will be appreciated by one of skill in the art, and with the help of this disclosure, the target CPO effluent temperature is the desired CPO effluent temperature, and the CPO effluent temperature (e.g., measured CPO effluent temperature, actual CPO effluent temperature) may or may not coincide with the target CPO effluent temperature. In embodiments where the CPO effluent temperature is different from the target CPO effluent temperature, one or more CPO operational parameters (e.g., CPO feed temperature; CPO pressure; CPO contact time; C/O molar ratio in the CPO reactant mixture; S/C molar ratio in the CPO reactant mixture; flow rate of cracking zone feed 60; etc.) can be adjusted (e.g., modified) in order for the CPO effluent temperature to match (e.g., be the same with, coincide with) the target CPO effluent temperature. CPO reaction zone 100 can be operated under any suitable operational parameters that can provide for a syngas 15 with a desired composition (e.g., a syngas with a desired $H_2$/CO molar ratio; a syngas with a desired $CO_2$ content; etc.).

The CPO reaction zone 100 can be characterized by a CPO feed temperature of from about 25° C. to about 600° C., alternatively from about 25° C. to about 500° C., alternatively from about 25° C. to about 400° C., alternatively from about 50° C. to about 400° C., or alternatively from about 100° C. to about 400° C. In embodiments where the CPO reactant mixture comprises steam, the CPO feed temperature can be as high as about 600° C., alternatively about 575° C., alternatively about 550° C., or alternatively about 525° C. In embodiments where the CPO reactant mixture does not comprise steam, the CPO feed temperature can be as high as about 450° C., alternatively about 425° C., alternatively about 400° C., or alternatively about 375° C.

The CPO reaction zone 100 can be characterized by a CPO effluent temperature (e.g., target CPO effluent temperature; (target) syngas 15 temperature) of equal to or greater than about 300° C., about 600° C., about 700° C., about 750° C., about 800° C., or about 850° C., alternatively from about 300° C. to about 1,600° C., about 600° C. to about 1,400° C., about 600° C. to about 1,300° C., about 700° C. to about 1,200° C., about 750° C. to about 1,150° C., about 800° C. to about 1,125° C., or about 850° C. to about 1,100° C.

In an embodiment, the CPO reaction zone 100 can be characterized by any suitable reactor temperature and/or catalyst bed temperature. For example, the CPO reaction zone 100 can be characterized by a reactor temperature and/or catalyst bed temperature of equal to or greater than about 300° C., about 600° C., about 700° C., about 750° C., about 800° C., or about 850° C., alternatively from about 300° C. to about 1,600° C., about 600° C. to about 1,400° C., about 600° C. to about 1,300° C., about 700° C. to about 1,200° C., about 750° C. to about 1,150° C., about 800° C. to about 1,125° C., or about 850° C. to about 1,100° C.

The CPO reaction zone 100 can be operated under any suitable temperature profile that can provide for a syngas 15 with a desired composition (e.g., a syngas with a desired $H_2$/CO molar ratio; a syngas with a desired $CO_2$ content; etc.). The CPO reaction zone 100 can be operated under non-adiabatic conditions, isothermal conditions, near-isothermal conditions, etc. For purposes of the disclosure herein, the term "non-adiabatic conditions" refers to process conditions wherein a reaction zone is subjected to external heat exchange or transfer (e.g., the reaction zone is heated; or the reaction zone is cooled), which can be direct heat exchange and/or indirect heat exchange. As will be appreciated by one of skill in the art, and with the help of this disclosure, the terms "direct heat exchange" and "indirect heat exchange" are known to one of skill in the art. By contrast, the term "adiabatic conditions" refers to process conditions wherein a reaction zone is not subjected to external heat exchange (e.g., the reaction zone is not heated; or the reaction zone is not cooled). Generally, external heat exchange implies an external heat exchange system (e.g., a cooling system; a heating system) that requires energy input and/or output. As will be appreciated by one of skill in the art, and with the help of this disclosure, external heat transfer can also result from heat loss from the catalyst bed (or reactor) owing to radiation heat transfer, conduction heat transfer, convection heat transfer, and the like, or combinations thereof. For example, the catalyst bed can participate in heat exchange with the external environment, and/or with reactor zones upstream and/or downstream of the catalyst bed.

For purposes of the disclosure herein, the term "isothermal conditions" refers to process conditions (e.g., CPO operational parameters) that allow for a substantially constant temperature of the reaction zone and/or catalyst bed (e.g., isothermal temperature) that can be defined as a temperature that varies by less than about +10° C., about +9° C., about +8° C., about +7° C., alternatively less than about +6° C., about +5° C., about +4° C., about +3° C., about +2° C., or about +1° C. across the reaction zone and/or catalyst bed, respectively. Further, for purposes of the disclosure herein, the term "isothermal conditions" refers to process conditions (e.g., CPO operational parameters) effective for providing for a syngas 15 with a desired composition (e.g., a desired $H_2/CO$ molar ratio; a desired $CO_2$ content; etc.), wherein the isothermal conditions comprise a temperature variation of less than about +10° C. across the reaction zone and/or catalyst bed. In embodiments, the CPO reaction zone 100 can be operated under any suitable operational parameters that can provide for isothermal conditions.

For purposes of the disclosure herein, the term "near-isothermal conditions" refers to process conditions (e.g., CPO operational parameters) that allow for a fairly constant temperature of the reaction zone 100 and/or catalyst bed (e.g., near-isothermal temperature), which can be defined as a temperature that varies by less than about +100° C., about +90° C., about +80° C., about +70° C., about +60° C., about +50° C., about +40° C., about +30° C., about +20° C., about +10° C., about +9° C., about +8° C., about +7° C., about +6° C., about +5° C., about +4° C., about +3° C., about +2° C., or about +1° C. across the reactor and/or catalyst bed, respectively. In some embodiments, near-isothermal conditions allow for a temperature variation of less than about +50° C., about +25° C., or about +10° C. across the reactor and/or catalyst bed. Further, for purposes of the disclosure herein, the term "near-isothermal conditions" is understood to include "isothermal" conditions. Furthermore, for purposes of the disclosure herein, the term "near-isothermal conditions" refers to process conditions (e.g., CPO operational parameters) effective for providing for a syngas with a desired composition (e.g., a desired $H_2/CO$ molar ratio; a desired $CO_2$ content; etc.), wherein the near-isothermal conditions comprise a temperature variation of less than about +100° C. across the reaction zone and/or catalyst bed. In an embodiment, a process as disclosed herein can comprise conducting the CPO reaction under near-isothermal conditions to produce syngas, wherein the near-isothermal conditions comprise a temperature variation of less than about +100° C. across the CPO reaction zone 100 and/or catalyst bed. In embodiments, the CPO reaction zone 100 can be operated under any suitable operational parameters that can provide for near-isothermal conditions.

Near-isothermal conditions can be provided by a variety of process and catalyst variables, such as temperature (e.g., heat exchange or heat transfer), pressure, gas flow rates, reactor configuration, catalyst bed configuration, catalyst bed composition, reactor cross sectional area, feed gas staging, feed gas injection, feed gas composition, and the like, or combinations thereof. Generally, and without wishing to be limited by theory, the terms "heat transfer" or "heat exchange" refer to thermal energy being exchanged or transferred between two systems (e.g., two reaction zones and/or reactors, such as a CPO reaction zone and/or CPO reactor and a cracking zone and/or cracking reactor), and the terms "heat transfer" or "heat exchange" are used interchangeably for purposes of the disclosure herein.

According to this disclosure, achieving a target CPO effluent temperature and/or near-isothermal conditions can be provided by heat exchange or heat transfer. The heat exchange can comprise heating the reaction zone; and/or cooling the reaction zone. In an embodiment, achieving a target CPO effluent temperature and/or near-isothermal conditions can be provided by cooling the CPO reaction zone 100. In another embodiment, achieving a target CPO effluent temperature and/or near-isothermal conditions can be provided by heating the CPO reaction zone 100.

According to this disclosure, achieving a target CPO effluent temperature and/or near-isothermal conditions can comprise indirect heat exchange and/or direct heat exchange. As will be appreciated by one of skill in the art, and with the help of this disclosure, the terms "direct heat exchange" and "indirect heat exchange" are known to one of skill in the art. As utilized herein, heating of a stream (e.g., a cracking zone feed stream), a reaction zone (e.g., a cracking zone), or a reactor (e.g., a cracking reactor) via indirect heat transfer between the stream, the reaction zone, or the reactor and another stream (e.g., a CPO product effluent syngas), another reaction zone (e.g., a CPO reaction zone), or another reactor (e.g., a CPO reactor) indicates heating without direct contact of the contents of the stream, the reaction zone, or the reactor with the contents of the another stream, the another reaction zone, or the another reactor, while heating of a stream (e.g., a cracking zone feed stream), a reaction zone (e.g., a cracking zone), or a reactor (e.g., a cracking reactor) via direct heat transfer between the stream, the reaction zone, or the reactor and another stream (e.g., a CPO reaction zone effluent syngas), another reaction zone (e.g., a CPO reaction zone), or another reactor (e.g., a CPO reactor) indicates heating with direct contact of the contents of the stream, the reaction zone, or the reactor with the contents of the another stream, the another reaction zone, or the another reactor. According to this disclosure, achieving a target CPO effluent temperature and/or near-isothermal conditions is provided, at least in part, by indirect heat exchange between the CPO reaction zone 100 and the cracking zone 600, as detailed further hereinbelow.

The heat exchange can comprise external heat exchange, external coolant fluid cooling, reactive cooling, liquid $N_2$ cooling, cryogenic cooling, electric heating, electric arc heating, microwave heating, radiant heating, natural gas combustion, solar heating, infrared heating, use of a diluent in the CPO reactant mixture, and the like, or combinations thereof. For example, reactive cooling can be effected by carrying out an endothermic reaction in a cooling coil/jacket associated with (e.g., located in) a CPO reactor comprising the CPO reaction zone 100.

In some embodiments, achieving a target CPO effluent temperature and/or near-isothermal conditions can be provided by removal of process heat from the CPO reaction zone. In other embodiments, achieving a target CPO effluent temperature and/or near-isothermal conditions can be provided by supplying heat to the CPO reaction zone. As will be appreciated by one of skill in the art, and with the help of this disclosure, a CPO reaction zone may need to undergo both heating and cooling in order to achieve a target CPO effluent temperature and/or near-isothermal conditions.

In an embodiment, the heat exchange or heat transfer can comprise introducing a cooling agent, such as a diluent, into CPO reaction zone 100, to decrease the reactor temperature and/or the catalyst bed temperature, while increasing a temperature of the cooling agent and/or changing the phase of the cooling agent. The cooling agent can be reactive or non-reactive. The cooling agent can be in liquid state and/or in vapor state. As will be appreciated by one of skill in the art, and with the help of this disclosure, the cooling agent can act as a flammability retardant; for example by reducing the temperature inside the reaction zone, by changing the gas mixture composition, by reducing the combustion of hydrocarbons to $CO_2$; etc.

In some embodiments, CPO reactant mixture 10 can further comprise a diluent, wherein the diluent contributes to achieving a target CPO effluent temperature and/or near-isothermal conditions via heat exchange, as disclosed herein. The diluent can comprise water, steam, inert gases (e.g., argon), $N_2$, $CO_2$, and the like, or combinations thereof. Generally, the diluent is inert with respect to the CPO reaction, e.g., the diluent does not participate in the CPO reaction. However, and as will be appreciated by one of skill in the art, and with the help of this disclosure, some diluents (e.g., water, steam, $CO_2$, etc.) might undergo chemical reactions other than the CPO reaction within the CPO reaction zone 100, and can change the composition of the resulting syngas 15, as will be described in more detail later herein; while other diluents (e.g., $N_2$, argon (Ar)) might not participate in reactions that change the composition of the resulting syngas. As will be appreciated by one of skill in the art, and with the help of this disclosure, the diluent can be used to vary the composition of the resulting syngas 15. The diluent can be present in the CPO reactant mixture 10 in any suitable amount.

According to this disclosure, achieving a target CPO effluent temperature and/or near-isothermal conditions can be provided, at least in part, by the removal of process heat (Q) from the CPO reaction zone 100, e.g., cooling the CPO reaction zone 100, by heating a cracking zone 600. As will be appreciated by one of skill in the art, and with the help of this disclosure, a positive Q going "out" (by the direction of the arrow 13) represents that heat is being transferred from that particular reaction zone, e.g., that particular reaction zone is being cooled. For example, Q in FIG. 1 indicates that heat is being transferred from the CPO reaction zone 100 (e.g., the CPO reaction zone 100 is being cooled), to the cracking process in cracking zone 600. As will be appreciated by one of skill in the art, and with the help of this disclosure, a positive Q going "in" (by the direction of the arrow 13) represents that heat is being transferred to that particular reaction zone, e.g., that particular reaction zone is being heated.

According to this disclosure and detailed further hereinbelow, the heat transfer comprises cooling the CPO reaction zone 100 while heating the cracking zone 600 (e.g., a cracking reactor comprising cracking zone 600). In embodiments, the cracking zone 600 can produce ethylene by ethane cracking. In an embodiment, a cracking zone feed 60 can be fed to the cracking zone 600, wherein the cracking zone feed comprises second hydrocarbons, such as alkanes (e.g., ethane, propane, butanes, naphtha, and the like, or combinations thereof); wherein at least a portion of the second hydrocarbons undergoes an endothermic cracking reaction in the cracking zone 600 to produce a cracking zone product stream 63; and wherein the cracking zone product stream 63 comprises olefins (e.g., ethylene), $H_2$, and unreacted alkanes. Heat transfer integration of a CPO process with a cracking process is described in more detail in the U.S. Provisional Patent Application No. 62/787,620 filed Jan. 2, 2019 and entitled "Catalyst Activity Management in Catalytic Partial Oxidation" and U.S. Provisional Patent Application No. 62/793,606 filed Jan. 17, 2019 and entitled "Methanol Production Process from Syngas Produced by Catalytic Partial Oxidation Integrated with Cracking", the disclosure of each of which is hereby incorporated herein by reference in its entirety for purposes not contrary to this disclosure. Heat transfer integration of a CPO process with a cracking process is described in U.S. Provisional Patent Application No. 62/820,397 filed Mar. 19, 2019 entitled "An Integrated Direct Heat Transfer Process for the Production of Methanol and Olefins by Catalytic Partial Oxidation and Cracking", while heat transfer integration of a CPO process with a dehydrogenation process is described in U.S. Provisional Patent Application Nos. 62/810,631 filed Feb. 26, 2019 entitled, "An Integrated Direct Heat Transfer Process for the Production of Methanol and Olefins by Catalytic Partial Oxidation and Catalytic Selective Dehydrogenation"; and 62/810,633 filed Feb. 26, 2019, "Integrated Indirect Heat Transfer Process for the Production of Syngas and Olefins by Catalytic Partial Oxidation and Catalytic Selective Dehydrogenation", and the disclosure of each of which is hereby incorporated herein by reference in its entirety for purposes not contrary to this disclosure.

In some embodiments, the heat transfer (e.g., heat transfer that provides for achieving a target CPO effluent syngas 15 temperature and/or near-isothermal conditions) excludes heat transfer with the syngas effluent subsequent to the effluent syngas 15 exiting a common housing 150 in which the CPO reaction zone 100 is housed. In other embodiments, the heat transfer (e.g., heat transfer that provides for achieving a target CPO effluent syngas 15 temperature and/or near-isothermal conditions) can comprise heat transfer with the effluent syngas 15 subsequent to the effluent syngas 15 exiting the common housing 150.

The CPO reaction zone 100 can be characterized by a CPO pressure (e.g., reaction zone pressure measured at the reaction zone exit or outlet) of equal to or greater than about 1 barg, about 10 barg, about 20 barg, about 25 barg, about 30 barg, about 35 barg, about 40 barg, or about 50 barg, alternatively less than about 30 barg, alternatively less than about 25 barg, alternatively less than about 20 barg, alternatively less than about 10 barg, alternatively from about 1 barg to about 90 barg, alternatively from about 1 barg to about 70 barg, alternatively from about 1 barg to about 40 barg, alternatively from about 1 barg to about 30 barg, alternatively from about 1 barg to about 25 barg, alternatively from about 1 barg to about 20 barg, alternatively from about 1 barg to about 10 barg, alternatively from about 20 barg to about 90 barg, alternatively from about 25 barg to about 85 barg, or alternatively from about 30 barg to about 80 barg.

The CPO reaction zone 100 can be characterized by a CPO contact time of from about 0.001 milliseconds (ms) to about 5 seconds (s), alternatively from about 0.001 ms to about 1 s, alternatively from about 0.001 ms to about 100 ms, alternatively from about 0.001 ms to about 10 ms, alternatively from about 0.001 ms to about 5 ms, or alternatively from about 0.01 ms to about 1.2 ms. Generally, the contact time of a reaction zone comprising a catalyst refers to the average amount of time that a compound (e.g., a molecule of that compound) spends in contact with the catalyst (e.g., within the catalyst bed), e.g., the average amount of time that it takes for a compound (e.g., a molecule of that compound) to travel through the catalyst bed. For purposes of the disclosure herein the contact time of less than about 5 ms can be referred to as "millisecond regime" (MSR); and a CPO process or CPO reaction as disclosed herein characterized by a contact time of less than about 5 ms can be referred to as "millisecond regime"—CPO (MSR-CPO) process or reaction, respectively. In some embodiments, the CPO reaction zone 100 can be characterized by a contact time of from about 0.001 ms to about 5 ms, or alternatively from about 0.01 ms to about 1.2 ms.

All of the CPO operational parameters disclosed herein are applicable throughout all of the embodiments disclosed herein, unless otherwise specified. As will be appreciated by one of skill in the art, and with the help of this disclosure, each CPO operational parameter can be adjusted to provide for a desired syngas quality, such as a syngas with a desired composition (e.g., a syngas with a desired $H_2/CO$ molar ratio; a syngas with a desired $CO_2$ content; etc.). For example, the CPO operational parameters can be adjusted to provide for an increased $H_2$ content of the syngas 15. As another example, the CPO operational parameters can be adjusted to provide for a decreased $CO_2$ content of the syngas 15. As yet another example, the CPO operational parameters can be adjusted to provide for a decreased unreacted hydrocarbons (e.g., unreacted $CH_4$) content of the syngas 15.

In an embodiment, the CPO reactant mixture 10 can further comprise a diluent, such as water and/or steam, $CO_2$, $N_2$, argon, etc. The CPO reaction zone 100 can be operated under any suitable operational conditions (e.g., CPO operational parameters) that can provide for a CPO reaction zone effluent (e.g., syngas 15) with a desired composition (e.g., a desired $H_2/CO$ molar ratio; a desired $CO_2$ content; etc.); for example, the CPO reaction zone 100 can be operated with introducing water and/or steam, and optionally $CO_2$ to the CPO reaction zone 100.

When carbon is present in the reaction zone (e.g., coke; C produced as a result of a decomposition reaction as represented by equation (2)), water and/or steam diluent can react with the carbon and generate additional CO and $H_2$, for example as represented by equation (3):

$$C+H_2O \rightleftharpoons CO+H_2 \quad (3)$$

As will be appreciated by one of skill in the art, and with the help of this disclosure, the presence of water and/or steam in the CPO reaction zone 100 can decrease the amount of coke in the CPO reaction zone 100.

Further, and as will be appreciated by one of skill in the art, and with the help of this disclosure, water and/or steam can be used to vary the composition of the resulting CPO reaction zone effluent (e.g., syngas 15). Steam can react with methane, for example as represented by equation (4):

$$CH_4+H_2O \rightleftharpoons CO+3H_2 \quad (4)$$

In an embodiment, a diluent comprising water and/or steam can increase a $H_2$ content of the resulting CPO reaction zone effluent (e.g., syngas 15). For example, in embodiments where the CPO reactant mixture 10 comprises water and/or steam diluent, the resulting CPO reaction zone effluent (e.g., syngas 15) can be characterized by a $H_2$ to CO molar ratio that is increased when compared to a $H_2$ to CO molar ratio of a CPO reaction zone effluent (e.g., syngas 15) produced by an otherwise similar process conducted with a reactant mixture comprising hydrocarbons and $O_2$ without the water and/or steam diluent. Without wishing to be limited by theory, the reforming reaction (e.g., as represented by equation (4)) is an endothermic reaction. The reforming reaction as represented by equation (4) can remove a portion of the process heat (e.g., heat produced by the exothermic CPO reaction, for example as represented by equation (1)).

In the presence of water and/or steam in CPO reaction zone 100, CO can react with the water and/or steam to form $CO_2$ and $H_2$ via a water-gas shift (WGS) reaction, e.g., as represented by eqn. (5):

$$CO+H_2O \rightleftharpoons CO_2+H_2 \quad (5)$$

While the WGS reaction can increase the $H_2/CO$ molar ratio of the syngas produced by the CPO reaction zone 100, it also produces $CO_2$.

In an embodiment, the CPO reaction zone 100 can be operated at an S/C molar ratio in the CPO reactant mixture 10 of less than about 2.4:1, about 2:1, about 1.5:1, about 1:1, about 0.8:1, or about 0.5:1, alternatively from about 0.01:1 to less than about 2.4:1, alternatively from about 0.05:1 to about 2:1, about 0.1:1 to about 1.5:1, about 0.15:1 to about 1:1, or about 0.2:1 to about 0.8:1. As will be appreciated by one of skill in the art, and with the help of this disclosure, the steam that is introduced to the CPO reaction zone for use as a diluent in a CPO reaction as disclosed herein is present in significantly smaller amounts than the amounts of steam utilized in steam reforming (e.g., SMR) processes, and as such, a process for producing syngas as disclosed herein can yield a syngas with lower amounts of $H_2$ when compared to the amounts of $H_2$ in a syngas produced by steam reforming.

The S/C molar ratio in the CPO reactant mixture 10 can be adjusted based on the desired CPO effluent temperature (e.g., target CPO effluent temperature) in order to increase (e.g., maximize) the $H_2$ content of the CPO reaction zone effluent (e.g., syngas 15). As will be appreciated by one of skill in the art, and with the help of this disclosure, the reaction (4) that consumes steam in the CPO reaction zone 100 is preferable over the water-gas shift (WGS) reaction (5) in the CPO reaction zone 100, as reaction (4) allows for increasing the $H_2$ content of the CPO reaction zone effluent (e.g., syngas 15), as well as the M ratio of the CPO reaction zone effluent (e.g., syngas 15), wherein the M ratio is a molar ratio defined as $(H_2-CO_2)/(CO+CO_2)$. Further, and as will be appreciated by one of skill in the art, and with the help of this disclosure, reaction (4) converts water and CO to both $H_2$ and $CO_2$.

In an embodiment, the amount of methane that reacts according to reaction (3) in the CPO reaction zone 100 is less than the amount of methane that reacts according to reaction (1) in the CPO reaction zone 100. In an embodiment, less than about 50 mol %, alternatively less than about 40 mol %, alternatively less than about 30 mol %, alternatively less than about 20 mol %, or alternatively less than about 10 mol % of hydrocarbons (e.g., methane) react with steam in the CPO reaction zone 100.

Without wishing to be limited by theory, the presence of water and/or steam in the CPO reaction zone 100 changes the flammability of the CPO reactant mixture 10, thereby providing for a wider practical range of C/O molar ratios in the CPO reactant mixture 10. Further, and without wishing to be limited by theory, the presence of water and/or steam in the CPO reaction zone 100 allows for the use of lower C/O molar ratios in the CPO reactant mixture 10. Furthermore, and without wishing to be limited by theory, the presence of water and/or steam in the CPO reaction zone 100 allows for operating the CPO reaction zone 100 at relatively high pressures.

As will be appreciated by one of skill in the art, and with the help of this disclosure, the introduction of water and/or steam in the CPO reaction zone 100 can lead to increasing the amount of unreacted hydrocarbons in the CPO reaction zone effluent (e.g., syngas 15). Further, as will be appreciated by one of skill in the art, and with the help of this disclosure, methanol (MeOH or $CH_3OH$) production processes typically tolerate limited amounts of unreacted hydrocarbons in the syngas.

In some embodiments, the CPO reaction zone effluent (e.g., syngas 15) can comprise less than about 7.5 mol %, alternatively less than about 5 mol %, or alternatively less than about 2.5 mol % hydrocarbons (e.g., unreacted hydrocarbons, unreacted $CH_4$). In such embodiments, the CPO reaction zone effluent (e.g., syngas 15) can be produced in a CPO process that employs water and/or steam. In such embodiments, the CPO reaction zone effluent (e.g., syngas 15) can be used for methanol synthesis.

Further, since $O_2$ is present in the CPO reactant mixture 10, the carbon present in the reaction zone (e.g., coke; C produced as a result of a decomposition reaction as represented by equation (2)) can also react with $O_2$, for example as represented by equation (6):

$$C + O_2 \rightarrow CO_2 \qquad (6)$$

When carbon is present in the reaction zone (e.g., coke; C produced as a result of a decomposition reaction as represented by equation (2)), $CO_2$ (e.g., introduced to the CPO reaction zone 100 as part of the CPO reactant mixture 10 and/or produced by the reaction represented by equation (6)) can react with the carbon, for example as represented by equation (7):

$$C + CO_2 \rightleftharpoons 2CO \qquad (7)$$

thereby decreasing the amount of $CO_2$ in the resulting CPO reaction zone effluent (e.g., syngas 15). As will be appreciated by one of skill in the art, and with the help of this disclosure, the presence of $CO_2$ in the CPO reaction zone 100 can decrease the amount of coke in the CPO reaction zone 100.

Furthermore, $CO_2$ can react with methane in a dry reforming reaction, for example as represented by equation (8):

$$CH_4 + CO_2 \rightleftharpoons 2\,CO + 2H_2 \qquad (8)$$

thereby decreasing the amount of $CO_2$ in the resulting CPO reaction zone effluent (e.g., syngas 15). Without wishing to be limited by theory, the dry reforming reaction (e.g., as represented by equation (8)) is an endothermic reaction (e.g., highly endothermic reaction). The dry reforming reaction can remove a portion of the process heat (e.g., heat produced by the exothermic CPO reaction, for example as represented by equation (1)).

In an embodiment, a diluent comprising $CO_2$ can increase a CO content of the resulting CPO reaction zone effluent (e.g., syngas 15). For example, in embodiments where the CPO reactant mixture 10 comprises $CO_2$ diluent, the CPO reaction zone effluent (e.g., syngas 15) can be characterized by a $H_2$ to CO molar ratio that is decreased when compared to a $H_2$ to CO molar ratio of a CPO reaction zone effluent (e.g., syngas) produced by an otherwise similar process conducted with a reactant mixture comprising hydrocarbons and $O_2$ without the $CO_2$ diluent. Without wishing to be limited by theory, $CO_2$ can react with coke inside the CPO reaction zone 100 and generate additional CO, for example as represented by equation (7). Further, and without wishing to be limited by theory, $CO_2$ can participate in a dry reforming of methane reaction, thereby generating additional CO and $H_2$, for example as represented by equation (8). Dry reforming of methane is generally accompanied by a reaction between $CO_2$ and $H_2$ which results in the formation of additional CO and water.

The use of $CO_2$ in the CPO reactant mixture 10 can advantageously decrease the amount of hydrocarbons converted to $CO_2$ in CPO reaction zone 100, for example via a combustion reaction. Without wishing to be limited by theory, and according to Le Châtelier's Principle, the equilibrium of hydrocarbons dry reforming reaction will be shifted towards consuming $CO_2$ with increasing the amount of $CO_2$ in the reactant mixture, thereby allowing for a higher amount of hydrocarbons to convert to syngas.

As will be appreciated by one of skill in the art, and with the help of this disclosure, and without wishing to be limited by theory, increasing the amount of $CO_2$ in CPO reactant mixture 10 can lead to an increased amount of CO in syngas 15, and thus to a lowered $H_2/CO$ molar ratio and/or a lowered M ratio of syngas 15. In some aspects, CPO reactant mixture 10 can comprise an amount of $CO_2$ effective to provide for a syngas 15 with a desired composition (e.g., a syngas with a desired $H_2/CO$ molar ratio; a syngas with a desired M ratio; a syngas with a desired $CO_2$ content; etc.). In aspects where the syngas 15 has a $H_2/CO$ molar ratio and/or an M ratio lower or much lower than the desired $H_2/CO$ molar ratio and/or the desired M ratio, respectively, the syngas 15 can be contacted with an increased amount of $H_2$ (e.g., $H_2$ stream 73), such as an amount of $H_2$ (e.g., $H_2$ stream 73) effective to provide for a hydrogen-enriched syngas 16 with a desired composition (e.g., a syngas with a desired $H_2/CO$ molar ratio; a syngas with a desired M ratio; a syngas with a desired $CO_2$ content; etc.). In aspects where the syngas 15 has a $H_2/CO$ molar ratio and/or an M ratio lower or slightly lower than the desired $H_2/CO$ molar ratio and/or the desired M ratio, respectively, the syngas 15 can be contacted with a decreased amount of $H_2$ (e.g., $H_2$ stream 73), such as an amount of $H_2$ (e.g., $H_2$ stream 73) effective to provide for a hydrogen-enriched syngas 16 with a desired composition (e.g., a syngas with a desired $H_2/CO$ molar ratio; a syngas with a desired M ratio; a syngas with a desired $CO_2$ content; etc.). As will be appreciated by one of skill in the art, and with the help of this disclosure, when the syngas 15 has a relatively higher $H_2/CO$ molar ratio and/or M ratio, it may not be necessary to use the entire amount of available $H_2$ (e.g., $H_2$ stream 73), and it may suffice to use only a portion of the available $H_2$ (e.g., $H_2$ stream 73).

In aspects where the CPO reactant mixture 10 comprises both steam and $CO_2$, the CPO reaction zone 100 can be operated at a steam to $CO_2$ ($S/CO_2$) molar ratio in the CPO reactant mixture 10 of less than about 100,000:1, about 50,000:1, about 10,000:1, about 5,000:1, about 1,000:1, or about 500:1, alternatively from about 0.1:1 to about 100, 000:1, about 0.2:1 to about 50,000:1, about 1:1 to about 10,000:1, about 5:1 to about 5,000:1, about 10:1 to about 1,000:1, or about 25:1 to about 500:1.

As will be appreciated by one of skill in the art, and with the help of this disclosure, a $CO_2$-lean syngas has a higher M ratio than a $CO_2$-rich syngas: the lower the $CO_2$ content of the syngas, the higher the M ratio of the syngas. The $CO_2$ content of the syngas can be adjusted as described in more detail in the co-pending U.S. Provisional Patent Application 62/787,574 filed Jan. 2, 2019 and entitled "Hydrogen Enrichment in Syngas Produced via Catalytic Partial Oxidation"; which is hereby incorporated herein by reference in its entirety for purposes not contrary to this disclosure.

In an embodiment, a CPO reaction zone effluent (e.g., syngas 15) can be recovered from the CPO reaction zone 100, wherein the CPO reaction zone effluent (e.g., syngas 15) comprises $H_2$, CO, water, $CO_2$, and unreacted hydrocarbons (e.g., unreacted first hydrocarbons, unreacted methane, optionally unreacted second hydrocarbons). The CPO reaction zone effluent syngas 15 as disclosed herein can be characterized by a $H_2/CO$ molar ratio of greater than about 1.3, about 1.4, about 1.5, about 1.6, about 1.7, about 1.8, about 1.9, or about 2.0. In some embodiments, the CPO reaction zone effluent syngas 15 as disclosed herein can be characterized by a $H_2/CO$ molar ratio of from about 1.3 to about 2.3, about 1.4 to about 2.3, about 1.5 to about 2.3, about 1.6 to about 2.3, about 1.7 to about 2.2, or about 1.8 to about 2.1. In an embodiment, the CPO reaction zone effluent syngas 15 can be characterized by an M ratio of equal to or greater than about 1.3, about 1.4, about 1.5, about 1.6, about 1.7, or about 1.8, from about 1.3 to about 2.3, alternatively from about 1.4 to about 2.3, alternatively from about 1.5 to about 2.3, alternatively from about 1.6 to about 2.3, alternatively from about 1.7 to about 2.2, or alternatively from about 1.8 to about 2.2.

In some embodiments, CPO reaction zone syngas 15 can be used in a downstream process (e.g., methanol production) without further processing to enrich the $H_2$ content of CPO reaction zone effluent syngas 15.

In other embodiments, the CPO reaction zone effluent syngas 15 can be further processed prior to using the CPO reaction zone effluent syngas 15 in a downstream process, such as methanol production. The CPO reaction zone effluent syngas 15 can be processed to enrich its $H_2$ content; for example by contacting the CPO reaction zone effluent syngas 15 with additional (e.g., supplemental) $H_2$ (e.g., $H_2$ stream 73, described further hereinbelow).

As will be appreciated by one of skill in the art, and with the help of this disclosure, although the CPO reaction zone effluent syngas 15 can be characterized by a $H_2/CO$ molar ratio of greater than about 1.8, which can be appropriate for methanol synthesis, the CPO reaction zone effluent syngas 15 can be processed to further increase its $H_2$ content. Further, as will be appreciated by one of skill in the art, and with the help of this disclosure, the CPO reaction zone effluent syngas 15 can be subjected to minimal processing, such as the recovery of unreacted hydrocarbons, diluent, water, etc., without substantially changing the $H_2/CO$ molar ratio of the CPO reaction zone effluent syngas 15. For example, water can be condensed and separated from the CPO reaction zone effluent syngas 15, e.g., in a condenser.

In an embodiment, a process as disclosed herein can further comprise (i) recovering at least a portion of the unreacted hydrocarbons (e.g., unreacted first hydrocarbons, optionally unreacted methane, optionally unreacted second hydrocarbons) from the CPO reaction zone effluent syngas 15 to yield recovered hydrocarbons, and (ii) recycling at least a portion of the recovered hydrocarbons to the CPO reaction zone 100. As will be appreciated by one of skill in the art, and with the help of this disclosure, although fairly high conversions can be achieved in CPO processes (e.g., conversions of equal to or greater than about 90%), the unconverted hydrocarbons could be recovered and recycled back to the CPO reaction zone 100. In some embodiments, at least a portion of the recovered hydrocarbons can be used as fuel (e.g., to preheat the CPO reactant mixture; to heat the cracking zone 600) and/or fed to the cracking zone 600.

In an embodiment, the CPO reaction zone effluent syngas 15 can have a $CO_2$ content of less than about 7 mol %, about 6 mol %, about 5 mol %, about 4 mol %, about 3 mol %, about 2 mol %, or about 1 mol %, alternatively from about 0.1 mol % to about 7 mol %, about 0.25 mol % to about 5 mol %, or about 0.5 mol % to about 3 mol %. For example, side reactions as represented by eqns. (7) and/or (8) could lead to a CPO reaction zone effluent syngas 15 that has a $CO_2$ content of about 0.1 mol % to about 7 mol %.

In an embodiment, the CPO reaction zone effluent syngas 15 can have a hydrocarbon content of less than about 10 mol %, about 7.5 mol %, about 5 mol %, about 4 mol %, about 3 mol %, about 2 mol %, about 1 mol %, about 0.1 mol %, or about 0.01 mol %.

With reference back to the embodiment of FIG. 1, a process as disclosed herein comprises a step of feeding a cracking zone feed 60 to a cracking zone 600 to produce a cracking zone product stream 63. In some embodiments, cracking zone product stream 63 can comprise olefins, such as ethylene, propene, butenes, and the like, or combinations thereof, along with $H_2$ and other hydrocarbons. Cracking zone product stream 63 can further comprise other unsaturated hydrocarbons, such as butadiene, $C_{5-6}$ olefins, $C_{6-8}$ aromatic hydrocarbons, etc. For example, cracking zone product stream 63 can comprise olefins and other unsaturated hydrocarbons, in addition to $H_2$. The cracking zone 600 can comprise any suitable cracking zone configured to convert saturated hydrocarbons (e.g., alkanes) into olefins. For example, cracking zone 600 can comprise any suitable cracking zone configured to convert cracking zone feed 60 comprising second hydrocarbons (e.g., saturated hydrocarbons, alkanes) into a cracking zone product stream 63 comprising olefins. Nonlimiting examples of cracking zones (e.g., cracking reactors) suitable for use in the present disclosure include a thermal cracking zone (e.g., a thermal cracking reactor), a catalytic cracking zone (e.g., a catalytic cracking reactor), a steam cracking zone (e.g., steam cracking reactor), and the like, or combinations thereof. As will be appreciated by one of skill in the art, and with the help of this disclosure, thermal cracking processes, catalytic thermal processes, steam cracking processes, and the like, or combinations thereof are known to one of skill in the art.

Without wishing to be limited by theory, cracking refers to the endothermic reaction that converts alkanes into olefins and $H_2$. Generally, as will be appreciated by one of skill in the art, and with the help of this disclosure, heat (e.g., thermal energy) has to be supplied to the cracking zone to enable the cracking reaction that produces olefins. According to this disclosure, at least a portion of the heat Q that is used by the cracking zone is supplied by CPO reaction zone 100, as disclosed herein. As will be appreciated by one of skill in the art, and with the help of this disclosure, the process heat from CPO reaction zone 100 may not be enough to supply all the heat necessary for cracking zone 600. In an aspect, a fuel stream can be combusted to supply the additional heat necessary for cracking zone 600.

In some embodiments, the cracking zone can comprise a gas cracking zone (e.g., within a gas cracking reactor). For example, in embodiments where the cracking zone feed 60 comprises ethane and/or propane, the cracking zone 600 can comprise a gas cracking zone. In other embodiments, the cracking zone can comprise a liquid cracking zone (e.g., within a liquid cracking reactor). For example, in embodiments where the cracking zone feed 60 comprises $C_4$ hydrocarbons, such as butanes, naphtha fractions (e.g., naphtha feedstocks), and the like, or combinations thereof; the cracking zone 600 can comprise a liquid cracking zone.

In an embodiment, the second hydrocarbons suitable for feeding to a cracking zone 600 as disclosed herein can comprise saturated hydrocarbons, such as alkanes. Nonlimiting examples of second hydrocarbons suitable for feeding to a cracking zone as disclosed herein can include alkanes, ethane, propane, butanes, naphtha, and the like, or combinations thereof. In some embodiments, the first hydrocarbons and the second hydrocarbons can be the same. For example, a naphtha feed can be introduced to a cracking zone 600, as well as to a CPO reaction zone 100. In other embodiments, the first hydrocarbons and the second hydrocarbons can be different. As another example, ethane (e.g., second hydrocarbons) can be introduced to a cracking zone 600 and methane (e.g., first hydrocarbons) can be introduced to a CPO reaction zone 100.

Figure 2A:
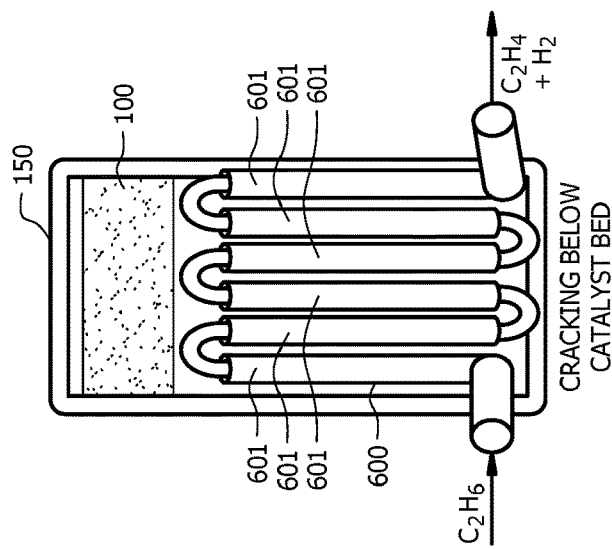
FIGS. 2A-2C display schematics of arrangements of a CPO reaction zone and a cracking zone, according to embodiments of this disclosure.
Figure 2B:
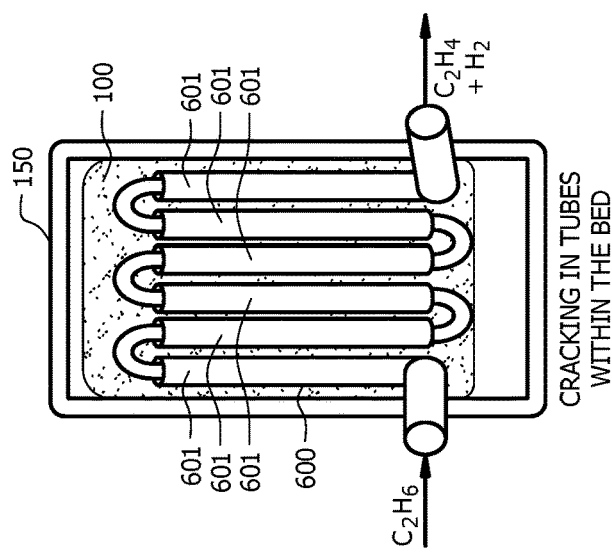
Figure 2C:
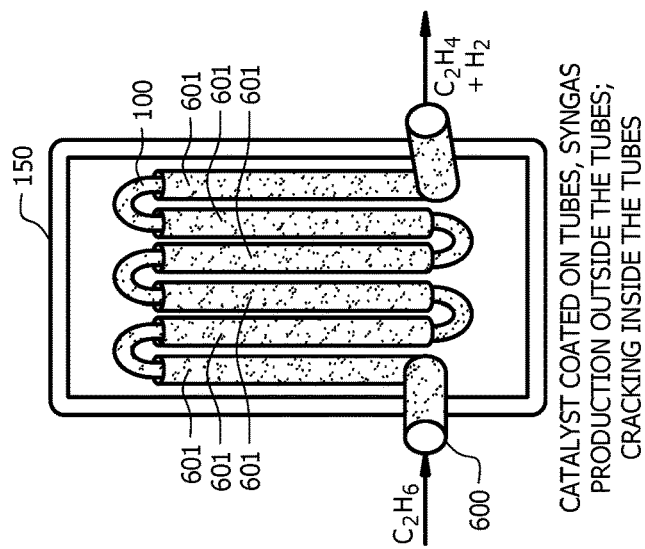

As will now be described with reference to the embodiments of FIGS. 2A-2C, in embodiments, a common housing 150 comprises both the CPO reaction zone 100 (such that the CPO catalyst is disposed within the common housing 150) and the cracking zone 600. In embodiments, the common housing 150 further comprises a cracking reactor disposed therein, wherein the cracking reactor is characterized by a cracking reactor outer surface and by a cracking reactor inner surface, and wherein the cracking reactor inner surface defines the cracking zone 600. In embodiments, the cracking reactor comprises one or more tubes (or "coils") 601 disposed within the common housing 150, and heating the cracking zone 600 comprises heating the second hydrocarbons within the one or more tubes 601 disposed within the common housing 150. As depicted in the embodiment of FIG. 2A, in embodiments, the CPO catalyst of the CPO reaction zone 100 is located above the one or more tubes 601. As depicted in the embodiment of FIG. 2B, in embodiments, the CPO catalyst of the CPO reaction zone 100 is located below the one or more tubes 601. As depicted in the embodiment of FIG. 2C, in embodiments, the CPO catalyst of the CPO reaction zone 100 is located around the one or more tubes and/or on the one or more tubes 601. Thus, in embodiments, the CPO catalyst is disposed within the common housing, and the CPO catalyst is located above the one or more tubes 601, below the one or more tubes 601, around the one or more tubes 601, on the one or more tubes 601, or combinations thereof.

In embodiments, the common housing 150 further comprises a furnace zone wherein a fuel stream can be combusted in the furnace zone to provide for additional heat for the endothermic cracking reaction. In embodiments, heating the cracking zone 600 comprises heating the cracking zone feed 60 within a cracking reactor disposed within the common housing 150. In embodiments, the cracking reactor outer surface does not contact the CPO catalyst (e.g., configuration of FIG. 2A). In embodiments, the CPO reaction zone 100 and the cracking zone 600 are adjacent to each other, and the CPO reaction zone 100 and the cracking zone 600 do not spatially overlap (e.g., configuration of FIG. 2A). In embodiments, at least a portion of the cracking reactor outer surface contacts the CPO catalyst (e.g., configuration of FIGS. 2B-2C). In embodiments, the common housing 150 comprises a CPO catalyst bed disposed therein, wherein the CPO catalyst bed comprises the CPO catalyst, and at least a portion of the cracking reactor is disposed within the CPO catalyst bed (e.g., configuration of FIG. 2B). In embodiments, a layer of CPO catalyst coats at least a portion of the cracking reactor outer surface (e.g., configuration of FIG. 2C). In embodiments, the layer of CPO catalyst has a thickness of less than or equal to about 500, 400, 300, 200, or 100 micrometers (μm).

A flow control valve can be utilized to introduce the CPO reactant mixture 10 to CPO reaction zone 100 and/or a flow control valve can be utilized to introduce the cracking zone feed 60 to cracking zone 600. The flow of the cracking zone feed 60 can be regulated by a set temperature of CPO reaction zone 100. Should the temperature of CPO reaction zone 100 increase above the set temperature, flow of cracking zone feed 60 can be increased via the flow control valve on the cracking zone feed 60 to provide enhanced heat removal from the CPO reaction zone 100 (e.g., a CPO catalyst bed of CPO reaction zone 100), whereby the temperature of the CPO reaction zone 100 can be returned to the set CPO temperature. Should the temperature of CPO reaction zone 100 be less than the set temperature of the CPO reaction zone 100, the flow control valve on the cracking zone feed 60 can be closed, to reduce or eliminate the flow of the cracking zone feed 60 to cracking zone 600. In this manner, potential runaway of the CPO reaction zone 100 can be prevented, and, in embodiments, near-isothermal conditions within the CPO reaction zone 100 can be maintained. In embodiments, multiple cracking reactor tubes are utilized, such that one set of cracking tubes (e.g., one cracking zone) can be online in cracking mode while another is in decoking mode. The tubes 601 can be sized based on the oxidation throughput (e.g., the flow rate of the CPO reactant mixture 10) of the CPO reaction zone 100. In embodiments, the cracking zone 600 is characterized by a cracking zone temperature in the range of from about 400° C. to about 1,200° C., from about 600° C. to about 1,100° C., from about 600° C. to about 850° C., or less than or equal to about 1,200, 1,100, 1,000, 900, 800, 700, 600, 500, or 400° C.

The cracking zone product stream 63 can be further subjected to further purification or separation processes, for example for the recovery of one or more components. In embodiments, a separation unit can be utilized to separate a $H_2$ stream 73, an unreacted hydrocarbon (e.g., unreacted second hydrocarbons) stream 82, and an olefin stream 81 from cracking zone product stream 63. In embodiments, the separation unit can comprise a gas-liquid separation unit, a pressure swing adsorption (PSA) unit, a membrane separation unit, a cryogenic separation unit, an oil scrubber separation unit, a size exclusion unit, or combinations thereof. As depicted in the embodiment of FIG. 1, the separation unit can comprise a second $H_2$ recovery unit 700 and/or a separator 800. In embodiments, the process thus further comprises separating at least a portion of the cracking zone product stream 63 into a $H_2$ stream 73 and a hydrocarbons stream (HC stream) 74, wherein HC stream 74 comprises olefins and unreacted hydrocarbons. Second $H_2$ recovery unit 700 is configured to separate $H_2$ stream 73 from HC stream 74. HC stream 74 comprises a greater concentration of olefins (e.g., ethylene, as well as propene, butenes, etc.), methane, and unreacted second hydrocarbons (e.g., alkanes, ethane, propane, butanes, naphtha, and the like, or combinations thereof) than cracking zone product stream 63, while $H_2$ stream 73 comprises a greater concentration of $H_2$ than cracking zone product stream 63. In some embodiments, second $H_2$ recovery unit 700 can comprise any suitable separating unit that is configured to separate cracking zone product stream 63 into $H_2$ stream 73 and HC stream 74. For example, second $H_2$ recovery unit 700 can employ gas-liquid separation, distillation, cryogenic distillation, extractive distillation, selective adsorption, selective absorption, and the like, or combinations thereof. In embodiments, second $H_2$ recovery unit 700 can comprise a gas-liquid separator, a distillation column, a cryogenic distillation column, a trayed and/or packed separation column, a compressor, a heat exchanger, a cooling tower, a PSA unit, etc. In embodiments, second $H_2$ recovery unit 700 comprises a PSA. In embodiments, a PSA of second $H_2$ recovery unit 700 and first $H_2$ recovery unit 500 (described further hereinbelow) are the same PSA.

In an embodiment, for example as illustrated in FIG. 1, at least a portion 63a of the cracking zone product stream 63 can be introduced to a second $H_2$ recovery unit 700 (e.g., a gas-liquid separation unit, a PSA unit, a membrane separation unit, a cryogenic separation unit, and the like, or combinations thereof) to further enrich the $H_2$ content of the cracking zone product stream 63; e.g., to recover the $H_2$ from the cracking zone product stream 63.

In an embodiment, for example as illustrated in FIG. 1, at least a portion 63b of the cracking zone product stream 63 can be introduced to a first $H_2$ recovery unit 500 (e.g., a PSA unit, a membrane separation unit, a cryogenic separation unit, and the like, or combinations thereof) to further enrich the $H_2$ content of the cracking zone product stream 63; e.g., to recover the $H_2$ from the cracking zone product stream 63. In such embodiment, the cracking zone product stream 63 can be compressed prior to introducing to the first $H_2$ recovery unit 500. As will be appreciated by one of skill in the art, and with the help of this disclosure, methanol production loops operate at fairly elevated pressures (e.g. about 70 barg-100 barg), and as such streams (e.g., at least a portion 63b of the cracking zone product stream 63) that are introduced to a methanol reaction loop have to compressed to meet the pressure requirements of the methanol production loop.

In some embodiments, the first $H_2$ recovery unit 500 and the second $H_2$ recovery unit 700 can be or comprise the same $H_2$ recovery unit (e.g., the same PSA). In other embodiments, the first $H_2$ recovery unit 500 and the second $H_2$ recovery unit 700 can be or comprise different $H_2$ recovery units (e.g., different PSAs).

In some embodiments, at least a portion 63a of cracking zone product stream 63 can be separated into $H_2$ stream 73 and HC stream 74 in second $H_2$ recovery unit 700. $H_2$ stream 73 comprises at least a portion of the $H_2$ of cracking zone product stream 63, and optionally hydrocarbons (e.g., hydrocarbons that were present in cracking zone product stream 63, such as olefins (e.g., ethylene), unreacted second hydrocarbons (e.g., ethane, propane, butanes, naphtha)). HC stream 74 comprises at least a portion of the hydrocarbons (e.g., olefins (e.g., ethylene), unreacted second hydrocarbons (e.g., ethane, propane, butanes, naphtha)) of cracking zone product stream 63, and optionally $H_2$. In an aspect, the concentration of $H_2$ in $H_2$ stream 73 is greater than the concentration of $H_2$ in cracking zone product stream 63. In an aspect, the concentration of hydrocarbons in HC stream 74 is greater than the concentration of hydrocarbons in cracking zone product stream 63.

Figure 3:
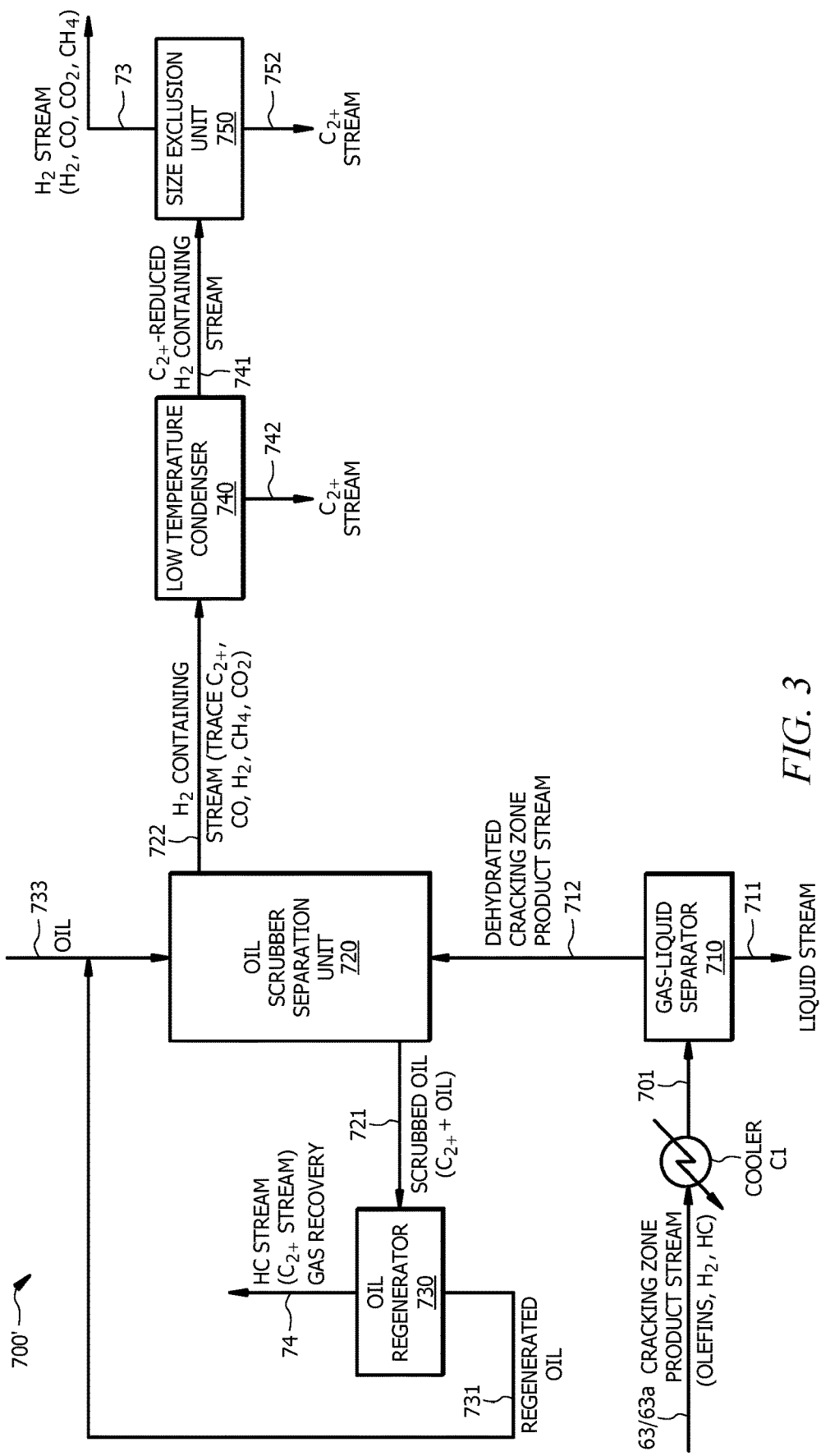
FIG. 3 displays a schematic of a separation unit, according to embodiments of this disclosure.

In embodiments, second $H_2$ recovery unit 700 comprises an oil scrubber separation unit and a size exclusion unit. Such a second $H_2$ recovery unit 700 can further comprise a cooler, a gas-liquid separator, an oil regenerator, and/or a low temperature condenser. For example, in the embodiment of FIG. 3, a second $H_2$ recovery unit 700' comprises a cooler C1, a gas-liquid separator 710, an oil scrubber separation unit 720, an oil regenerator 730, a low temperature condenser 740, and a size exclusion unit 750. In such embodiments, cracking zone product stream 63 or at least a portion 63a thereof (e.g., comprising cracking products (e.g., olefins), unreacted hydrocarbons, such as unreacted second hydrocarbons, $H_2$, etc.) can be scrubbed in oil scrubber separation unit 720. The cracking zone product stream or the portion thereof (63/63a) can be cooled in cooler C1 (e.g., to a temperature of less than or equal to about 100° C., alternatively less than or equal to about 80° C., alternatively less than or equal to about 60° C., alternatively from about 20° C. to about 100° C., alternatively from about 30° C. to about 80° C., or alternatively from about 40° C. to about 60° C.) to provide cooled, cracking zone product stream 701. Cooled, cracking zone product stream 701 can be introduced into gas-liquid separator 710, wherein liquid stream 711 can be separated from the cooled, cracking zone product stream 701 to provide dehydrated cracking zone product stream 712.

The gas-liquid separator 710 of the second $H_2$ recovery unit 700/700' can comprise any suitable gas-liquid separator configured to separate the cooled, cracking zone product stream 701 into a liquid stream 711 comprising water and a dehydrated cracking zone product stream 712, comprising a reduced water content relative to that of cooled, cracking zone product stream 701. For example, gas-liquid separator 710 can comprise a vapor-liquid separator, flash drum, knock-out drum, knock-out pot, compressor suction drum, etc. Liquid stream 711 can be recovered from the gas-liquid separator 710 as a bottoms stream. Liquid stream 711 recovered from the gas-liquid separator 710 can comprise water, $C_5$ hydrocarbons, such as pentane, pentenes, hexanes, hexenes, benzene, toluene, xylene, and the like, or combinations thereof. As will be appreciated by one of skill in the art, and with the help of this disclosure, liquid stream 711 recovered from the gas-liquid separator 710 can further comprise trace amounts of $C_{4-}$ hydrocarbons, such as butanes, butenes, butadiene, etc. The dehydrated cracking zone product stream 712 can comprise less than about 5 mol %, about 4 mol %, about 3 mol %, about 2 mol %, about 1 mol %, about 0.5 mol %, about 0.1 mol %, about 0.05 mol %, or about 0.01 mol % water, in addition to cracking zone product hydrocarbons (e.g., $C_2$, $C_3$, and $C_4$ hydrocarbons, with some optional trace amounts of $C_5$ hydrocarbons), including olefins, methane, ethane, propane, unreacted second hydrocarbons, $H_2$, CO, and/or $CO_2$. In embodiments (e.g., wherein cracking zone product stream 63/63a does not comprise significant amounts of water), cooler C1 and/or gas-liquid separator 710 may be absent from second $H_2$ recovery unit 700/700'.

In some aspects, the liquid stream 711 can be further introduced to a liquid-liquid separator, wherein the liquid-liquid separator can comprise any suitable liquid-liquid separator configured to separate the liquid stream 711 into an aqueous phase stream comprising water, and an oil phase stream comprising hydrocarbons. For example, the liquid-liquid separator can comprise a horizontal gravity settling tank, a vertical gravity settling tank, a coalescer, a membrane separator, and the like, or combinations thereof. In some aspects, the aqueous phase stream can comprise water, and traces of $C_{4-}$ hydrocarbons, such as butanes, butenes, butadiene, and the like, or combinations thereof. The oil phase stream can comprise $C_5$ hydrocarbons, such as pentane, pentenes, hexanes, hexenes, benzene, toluene, xylene, and the like, or combinations thereof; and traces of water and/or $C_{4-}$ hydrocarbons, such as butanes, butenes, butadiene, etc.

In some aspects, the gas-liquid separator 710 can comprise a gas-liquid-liquid separator. The gas-liquid-liquid separator can comprise any suitable gas-liquid-liquid separator configured to separate the cooled, cracking zone product stream 701 into a dehydrated cracking zone product stream 712, an aqueous phase stream comprising water, and an oil phase stream comprising hydrocarbons. For example, the gas-liquid-liquid separator can comprise a gas-liquid separator (e.g., a vapor-liquid separator, flash drum, knock-out drum, knock-out pot, compressor suction drum, etc.) integrated with a liquid-liquid separator (e.g., a horizontal gravity settling tank, a vertical gravity settling tank, a coalescer, a membrane separator, and the like, or combinations thereof). The dehydrated cracking zone product stream 712 recovered from the gas-liquid-liquid separator can comprise less than about 5 mol %, about 4 mol %, about 3 mol %, about 2 mol %, about 1 mol %, about 0.5 mol %, about 0.1 mol %, about 0.05 mol %, or about 0.01 mol % water, in addition to cracking zone product hydrocarbons, including olefins, methane, ethane, propane, unreacted second hydrocarbons, $H_2$, CO, and/or $CO_2$. The aqueous phase stream recovered from the gas-liquid-liquid separator can comprise water, and traces of $C_{4-}$ hydrocarbons, such as butanes, butenes, butadiene, and the like, or combinations thereof. The oil phase stream recovered from the gas-liquid-liquid separator can comprise $C_5$ hydrocarbons, such as pentane, pentenes, hexanes, hexenes, benzene, toluene, xylene, and the like, or combinations thereof; and traces of water and/or $C_{4-}$ hydrocarbons, such as butanes, butenes, butadiene, etc.

Within oil scrubber separation unit 720, the cracking zone product stream 63/63a or the dehydrated cracking zone product stream 712 is contacted with a scrubbing oil in oil stream 733 to provide a hydrogen containing stream 722 and a scrubbed oil stream 721 comprising spent oil (e.g., scrubbing oil and $C_2$ hydrocarbons scrubbed from cracking zone product stream 63/63a or the dehydrated cracking zone product stream 712 introduced thereto. The hydrogen containing stream 722 can comprise trace amounts of $C_2$ hydrocarbons, along with $H_2$, $CH_4$, CO, and $CO_2$.

An oil regenerator 730 can be utilized to separate a regenerated oil stream 731 from hydrocarbon stream 74, comprising cracking products, including, olefins and unreacted hydrocarbons (e.g., unreacted second hydrocarbons). The regenerated oil stream 731 can be reintroduced into oil scrubber separation unit 720, for example, via oil stream 733.

Remaining hydrocarbons can be removed from hydrogen containing stream 722, to provide $H_2$ stream 73. For example, in embodiments, hydrogen containing stream 722 can be subjected to low temperature (e.g., less than or equal to about 10° C., alternatively less than or equal to about 5° C., alternatively less than or equal to about 0° C., alternatively from about −40° C. to about 10° C., alternatively from about −32° C. to about 5° C., or alternatively from about −20° C. to about 0° C.) condensing in a low temperature condenser 740, to separate a $C_2$ stream 742 from a $C_{2+}$-reduced hydrogen containing stream 741. $C_{2+}$-reduced hydrogen containing stream 741 can be subjected to size exclusion in a size exclusion unit 750, to provide $H_2$ stream 73 and another $C_2$ stream 752. Low temperature condenser 740 and size exclusion unit 750 can comprise any low temperature condenser and size exclusion unit known to those of skill in the art, and with the help of this disclosure, to be operable to provide the noted separations of the $C_2$ streams 742 and 752, respectively. For example, size exclusion unit 750 can comprise any suitable number of size exclusion units, such as 1, 2, 3, 4, 5, or more size exclusion units. In embodiments, the $C_{2+}$ streams 742 and/or 752 can be combined with HC stream 74, for example, prior to subsequent processing and/or utilization of HC stream 74.

In an embodiment, the HC stream 74 can be further subjected to one or more separation steps to recover the olefins. For example, ethylene can be recovered from the HC stream 74, wherein ethylene can be further used, for example, in a polymerization process. In an embodiment, at least a portion 74a of the HC stream 74 is introduced into separator 800, which is configured to separate the at least a portion 74a of the HC stream 74 into an olefin stream 81, wherein the olefins stream 81 comprises at least a portion of the olefins in HC stream 74 (e.g., ethylene, propylene, butenes) and an unreacted hydrocarbon stream 82, wherein the unreacted hydrocarbons stream 82 comprises at least a portion of the unreacted hydrocarbons (e.g., second hydrocarbons) in HC stream 74. In embodiments, olefins stream 81 can comprise olefins, such as ethylene and/or propylene. In an embodiment, unreacted hydrocarbons stream 82 can comprise methane, ethane, propane, and the like, or combinations thereof. In some aspects, the unreacted hydrocarbons stream 82 can further comprise trace amounts of $H_2$, $CO_2$, CO, and the like, or combinations thereof. Separator 800 can effect the separation via any suitable separation technique, such as, without limitation, distillation, cryogenic distillation, extractive distillation, selective adsorption, selective absorption, and the like, or combinations thereof.

As will be appreciated by one of skill in the art, and with the help of this disclosure, the composition of cracking zone product stream 63, the composition of HC stream 74, the composition of unreacted hydrocarbons stream 82, and the composition of olefins stream 81 are all dependent on a variety of factors, such as the composition of the cracking zone feed 60, the type of cracking zone 600, the operating conditions for cracking zone 600, etc.

In embodiments, a process of this disclosure comprises recycling at least a portion of the HC stream 74, at least a portion of $C_2$ stream 742, at least a portion of $C_2$ stream 752, and/or at least a portion of unreacted hydrocarbons stream 82 to the cracking zone 600 and/or to CPO reaction zone 100.

In embodiments, at least a portion of the unreacted hydrocarbon stream 82 is introduced into the cracking zone 600, at least a portion of the unreacted hydrocarbon stream 82 is introduced into the CPO reaction zone 100, at least a portion of the unreacted hydrocarbon stream 82 is utilized as a fuel to heat the cracking zone 600 (e.g., is introduced into a furnace within common housing 150), and/or at least a portion of the unreacted hydrocarbon stream 82 is utilized as a fuel to heat the CPO reactant mixture 10.

In an embodiment, at least a portion of the HC stream 74 can be fed to the CPO reaction zone 100, for example via the CPO reactant mixture 10. In an embodiment, at least a portion of the HC stream 74 can be used as fuel (e.g., to preheat the CPO reactant mixture; to heat the cracking zone 600) and/or fed to the cracking zone 600. The HC stream 74 can provide for additional (e.g., supplemental) hydrocarbons to undergo a CPO reaction in the CPO reaction zone 100.

In embodiments where a portion of the unreacted hydrocarbons 82 and/or a portion of the HC stream 74 is introduced to CPO reaction zone 100, the M ratio and/or the $H_2/CO$ molar ratio of syngas 15 can be greater than the M ratio and/or the $H_2/CO$ molar ratio, respectively of a syngas produced by an otherwise similar process that feeds a CPO reactant mixture without the portion of unreacted hydrocarbons 82 and/or HC stream 74 to a CPO reaction zone 100. In embodiments, at least a portion of hydrocarbon stream 74 and/or at least a portion of unreacted hydrocarbons 82 can be used as fuel (e.g., to preheat the CPO reactant mixture 10; to heat the cracking zone 600) and/or fed to the cracking zone 600.

In an embodiment, at least a portion of the unreacted hydrocarbons 82 and/or at least a portion of the HC stream 74 can be recycled to the cracking zone 600, for example via the cracking zone feed 60. In an embodiment, at least a portion of the unreacted hydrocarbons 82 and/or at least a portion of the HC stream 74 can be used as fuel, for example for heating the cracking zone 600 and/or preheating the CPO reactant mixture 10. As some crackers (e.g., cracking zones 600) may have a maximum olefin feed limit (e.g., 5, 4, 3, 2, or 1 wt %), when at least a portion of HC stream 74 is recycled to cracking zone 600 via cracking zone feed 60, the at least a portion recycled is selected to maintain the olefin content of the cracking zone feed 60 below said maximum olefin feed limit.

In an embodiment, at least a portion of the $H_2$ stream 73 can be contacted with at least a portion of the CPO reaction zone effluent syngas 15 to produce a hydrogen-enriched syngas 16, for example as illustrated in FIG. 1. The $H_2$/CO molar ratio of the hydrogen-enriched syngas 16 is greater than the $H_2$/CO molar ratio of the CPO reaction zone effluent syngas 15. The M ratio of the hydrogen-enriched syngas 16 is greater than the M ratio of the CPO reaction zone effluent syngas 15.

The hydrogen-enriched syngas 16 as disclosed herein can be characterized by a $H_2$/CO molar ratio of greater than about 1.7, about 1.8, about 1.9, about 2.0, about 2.1, about 2.2, about 2.3, about 2.4, or about 2.5. In an embodiment, the hydrogen-enriched syngas 16 as disclosed herein can be characterized by an M ratio of equal to or greater than about 1.8, alternatively equal to or greater than about 2.0, alternatively equal to or greater than about 2.1, alternatively greater than about 2.2, alternatively greater than about 2.3, alternatively greater than about 2.4, alternatively greater than about 2.5, alternatively from about 1.8 to about 2.5, alternatively from about 1.8 to about 2.4, alternatively from about 1.9 to about 2.3, or alternatively from about 2.0 to about 2.2.

In an embodiment, the hydrogen-enriched syngas 16 as disclosed herein can comprise $CO_2$ in an amount of an amount of less than about 7 mol %, about 6 mol %, 5 mol %, about 4 mol %, about 3 mol %, about 2 mol %, or about 1 mol %, alternatively from about 0.1 mol % to about 7 mol %, about 0.25 mol % to about 5 mol %, or about 0.5 mol % to about 3 mol %. The amount of $CO_2$ in the hydrogen-enriched syngas 16 can be less than the amount of $CO_2$ in the syngas 15. As will be appreciated by one of skill in the art, and with the help of this disclosure, the $H_2$ stream 73 recovered from the cracking zone 600 can have a reduced $CO_2$ content, as compared to an effluent stream from the CPO reaction zone 100. Consequently, combining $H_2$ stream 73 recovered from the cracking zone 600 with an effluent stream syngas 15 from the CPO reaction zone 100 can result in a stream with a reduced $CO_2$ content as compared to the effluent stream syngas 15 from the CPO reaction zone 100.

In an embodiment, the hydrogen-enriched syngas 16 as disclosed herein can comprise hydrocarbons in an amount of an amount of less than about 5 mol %, about 4 mol %, about 3 mol %, about 2 mol %, about 1 mol %, about 0.1 mol %, or about 0.01 mol %. The amount of hydrocarbons in the hydrogen-enriched syngas 16 can be less than the amount of hydrocarbons in the CPO reaction zone effluent syngas 15. As will be appreciated by one of skill in the art, and with the help of this disclosure, the $H_2$ stream 73 recovered from the cracking zone 600 can have a reduced hydrocarbons content, as compared to an effluent stream syngas 15 from the CPO reaction zone 100. Consequently, combining $H_2$ stream 73 recovered from the cracking zone 600 with an effluent stream syngas 15 from the CPO reaction zone 100 can result in a hydrogen-enriched syngas stream 16 with a reduced hydrocarbons content as compared to the effluent stream syngas 15 from the CPO reaction zone 100.

In embodiments where the syngas (e.g., syngas 15; $H_2$-enriched syngas 16) is characterized by an M ratio of from about 1.8 to about 2.2, the syngas can be further used for methanol production.

In an embodiment, a process for producing methanol as disclosed herein can comprise a step of introducing at least a portion of the syngas 15 and/or at least a portion of the hydrogen-enriched syngas 16 to the methanol reactor 200 to produce a methanol reactor effluent stream 30; wherein the methanol reactor effluent stream 30 comprises methanol, water, $H_2$, CO, $CO_2$, and hydrocarbons. The methanol reactor 200 can comprise any reactor suitable for a methanol synthesis reaction from CO and $H_2$, such as for example a trickle bed reactor, a fluidized bed reactor, a slurry reactor, a loop reactor, a cooled multi tubular reactor, and the like, or combinations thereof.

Generally, CO and $H_2$ can be converted into $CH_3OH$, for example as represented by eqn. (9):

$$CO + H_2 \rightleftharpoons CH_3OH \quad (9)$$

$CO_2$ and $H_2$ can also be converted to methanol, for example as represented by equation (10):

$$CO_2 + 3H_2 \rightleftharpoons CH_3OH + H_2O \quad (10)$$

Without wishing to be limited by theory, the lower the $CO_2$ content of the syngas, the lower the amount of water produced in the methanol reactor 200. As will be appreciated by one of skill in the art, and with the help of this disclosure, syngas produced by SMR has a fairly high content of $H_2$ (as compared to the $H_2$ content of syngas produced by CPO), and a syngas with an elevated $H_2$ content can promote the $CO_2$ conversion to methanol, for example as represented by equation (10), which in turn can lead to an increased water content in a crude methanol stream (e.g., crude methanol stream 40).

$CH_3OH$ synthesis from CO, $CO_2$ and $H_2$ is a catalytic process, and is most often conducted in the presence of copper based catalysts. The methanol reactor 200 can comprise a methanol production catalyst, such as any suitable commercial catalyst used for methanol synthesis. Nonlimiting examples of methanol production catalysts suitable for use in methanol reactor 200 in the current disclosure include Cu, Cu/ZnO, Cu/ThO$_2$, Cu/Zn/Al$_2$O$_3$, Cu/ZnO/Al$_2$O$_3$, Cu/Zr, and the like, or combinations thereof.

In an embodiment, a process for producing methanol as disclosed herein can comprise a step of separating at least a portion of the methanol reactor effluent stream 30 into a crude methanol stream 40 and a vapor stream 50; wherein the crude methanol stream 40 comprises methanol and water; wherein the vapor stream 50 comprises $H_2$, CO, $CO_2$, and hydrocarbons (e.g., first hydrocarbons and/or second hydrocarbons). The methanol reactor effluent stream 30 can be separated into the crude methanol stream 40 and the vapor stream 50 in the gas-liquid separator 300, such as a vapor-liquid separator, flash drum, knock-out drum, knock-out pot, compressor suction drum, etc.

In an embodiment, a process for producing methanol as disclosed herein can comprise a step of separating at least a portion of the crude methanol stream 40 in distillation unit 400 into a methanol stream 45 and a water stream 46, wherein distillation unit 400 comprises one or more distillation columns. The water stream 46 comprises water and residual methanol. Generally, the one or more distillation columns can separate components of the crude methanol stream 40 based on their boiling points. As will be appreciated by one of skill in the art, and with the help of this disclosure, the higher the water content of the crude methanol stream 40, the more distillation columns are necessary to purify the methanol.

In an embodiment, the methanol stream 45 can comprise methanol in an amount of equal to or greater than about 95 wt. %, about 97.5 wt. %, about 99 wt. %, or about 99.9 wt. %, based on the total weight of the methanol stream 45.

In an embodiment, a process for producing methanol as disclosed herein can comprise a step of separating at least a portion of vapor stream 50 into a $H_2$ stream 51 and a residual gas stream 52, wherein the $H_2$ stream 51 comprises at least a portion of the $H_2$ of the vapor stream 50, and wherein the residual gas stream 52 comprises CO, $CO_2$, and hydrocarbons (e.g., first hydrocarbons and/or second hydrocarbons). The vapor stream 50 can be separated into the $H_2$ stream 51 and the residual gas stream 52 in the first $H_2$ recovery unit 500, such as a PSA unit, a membrane separation unit, a cryogenic separation unit, and the like, or combinations thereof. In some embodiments, at least a portion 63b of the cracking zone product stream 63 can be introduced to the first $H_2$ recovery unit 500.

In an embodiment, a process for producing methanol as disclosed herein can comprise recycling at least a portion 51a of the $H_2$ stream 51 to the methanol reactor 200; for example via a syngas feed to the methanol reactor 200. In some aspects, at least a portion 51a of the $H_2$ stream 51 can be contacted with at least a portion of the hydrogen-enriched syngas 16 to yield a methanol reactor feed stream 21, wherein at least a portion of the methanol reactor feed stream 21 can be introduced to the methanol reactor 200 to produce methanol. In such aspects, the methanol reactor feed stream 21 can be characterized by an M ratio of from about 4 to about 17, alternatively from about 5 to about 15, alternatively from about 6 to about 12, or alternatively from about 7 to about 10. In some embodiments, at least a portion of the residual gas stream 52 can be purged. In other embodiments, at least a portion of the residual gas stream 52 can be used as fuel, for example for pre-heating the CPO reactant mixture 10, heating the cracking zone 600, and the like, or combinations thereof. In other embodiments, at least a portion 52a of the residual gas stream 52 can be fed to the CPO reaction zone 100. In yet other embodiments, at least a portion 52b of the residual gas stream 52 can be fed to the cracking zone 600.

In an embodiment, a process for producing methanol and olefins (e.g., ethylene) as disclosed herein can comprise the steps of: (a) feeding a catalytic partial oxidation (CPO) reactant mixture 10 to a CPO reaction zone 100; wherein the CPO reactant mixture 10 comprises $O_2$, first hydrocarbons, and optionally steam; wherein the CPO reaction zone 100 comprises a CPO catalyst; wherein at least a portion of the CPO reactant mixture 10 reacts under near-isothermal conditions, via an exothermic CPO reaction, in the CPO reaction zone 100 to produce syngas 15; wherein the near-isothermal conditions comprise a temperature variation of less than about ±100° C. across the CPO reaction zone 100 and/or a catalyst bed thereof, and wherein the catalyst bed comprises the CPO catalyst; wherein the syngas 15 comprises $H_2$, CO, $CO_2$, water, and unreacted first hydrocarbons, and wherein the syngas 15 is characterized by an M ratio of the syngas, wherein the M ratio is a molar ratio defined as $(H_2-CO_2)/(CO+CO_2)$; (b) feeding a cracking zone feed 60 to a cracking zone 600, wherein the cracking zone feed 60 comprises second hydrocarbons (e.g., ethane); wherein at least a portion of the cracking zone feed 60 undergoes an endothermic cracking reaction in the cracking zone 600 to produce a cracking zone product stream 63; wherein the cracking zone product stream 63 comprises olefins (e.g., ethylene), $H_2$, and unreacted second hydrocarbons (e.g., unreacted ethane); (c) cooling the CPO reaction zone 100; wherein cooling the CPO reaction zone 100 comprises heating the cracking zone 600 while cooling the CPO reaction zone 100 by (e.g., indirect) heat transfer between the CPO reaction zone 100 and the cracking zone 600; and wherein the heat transfer between the CPO reaction zone 100 and the cracking zone 600 provides for near-isothermal conditions in the CPO reaction zone 100; (d) separating at least a portion of the cracking zone product stream 63 in a separation unit (e.g., a separation unit comprising second $H_2$ recovery unit 700 and/or separator 800) into an olefin stream 81 (e.g., an ethylene stream), a $H_2$ stream 73, and an unreacted hydrocarbons stream 82 (e.g., unreacted second hydrocarbons, unreacted ethane); (e) optionally contacting at least a portion of the $H_2$ stream 73 with at least a portion of the syngas 15 to produce a hydrogen-enriched syngas 16, wherein the hydrogen-enriched syngas 16 is characterized by an M ratio greater than the M ratio of the syngas 15, and wherein the M ratio of the hydrogen-enriched syngas 16 is equal to or greater than about 1.7; (f) optionally recycling at least a portion of the unreacted hydrocarbons stream 82 (e.g., unreacted ethane) to the cracking zone 600 in step (b); and (g) introducing at least a portion of the syngas 15 and/or at least a portion of the hydrogen-enriched syngas 16 to a methanol reactor 200 to produce methanol. In such embodiment, the M ratio of the hydrogen-enriched syngas 16 can be equal to or greater than about 1.8, and the $H_2$/CO molar ratio of the hydrogen-enriched syngas 16 can be greater than about 2.0. In such embodiment, the second hydrocarbons can comprise ethane, the cracking zone 600 can comprises an ethane cracker, and the olefins can comprise ethylene.

In an embodiment, a process for producing syngas and olefins as disclosed herein can advantageously display improvements in one or more process characteristics when compared to an otherwise similar process that does not integrate a CPO reaction zone with a cracking zone. The process as disclosed herein can advantageously utilize a $H_2$ stream 73 separated from the cracking zone product 63 to increase the $H_2$ content of a CPO reaction zone effluent syngas 15.

As will be appreciated by one of skill in the art, and with the help of this disclosure, since the CPO reaction is exothermic, very little heat supply in the form of fuel combustion is needed (e.g., for pre-heating reactants in the reaction mixture that is supplied to a syngas generation section), when compared to conventional steam reforming. As such, the process for producing syngas as disclosed herein can advantageously generate less $CO_2$ through fuel burning, when compared to steam reforming. Further, the process as disclosed herein utilizes at least a portion of the process heat from the CPO reaction zone 100 to heat the cracking zone 600, thereby preventing run-away temperatures in the CPO reaction zone 100 (e.g., in a CPO catalyst bed), which could lead to catalyst de-activation. As will be appreciated by one of skill in the art, and with the help of this disclosure, operating the CPO reaction zone 100 at a relatively low C/O ratio (e.g., less than about 2:1) can lead to run-away temperatures, and thus removing heat from the CPO reaction zone 100 can advantageously enable operating the CPO reaction zone at relatively low C/O ratios.

In an embodiment, at least a portion of the cracking zone product stream 63, the HC stream 74, and/or the unreacted hydrocarbons stream 82 can be advantageously mixed into the CPO reactant mixture 10 such that the resulting CPO reactant mixture 10 has a $H_2$ content of less than about 20 mol %, or about 14 mol %, which allows for the hydrocarbons therein to be utilized in the CPO reaction.

In an embodiment, an existing $H_2$ separation unit (e.g., first $H_2$ recovery unit 500) in the methanol loop, or a second $H_2$ recovery unit 700 can be utilized to separate $H_2$ stream 73 from cracking zone product stream 63. The $H_2$ stream(s) (51, 73) recovered from $H_2$ separation units 500, 700 can be recycled advantageously (51a, 73) to the methanol loop inlet and unconverted hydrocarbons (e.g., in residual gas stream 52, HC stream 74, and/or unreacted hydrocarbons stream 82) can be advantageously recycled (e.g., via lines 52a, a line fluidly connecting HC stream 74 with CPO reaction zone 100, a line fluidly connecting unreacted hydrocarbon stream 82 with CPO reaction zone 100, respectively) to CPO reaction zone 100.

In an embodiment, a process for producing syngas and olefins as disclosed herein can advantageously comprise introducing at least a portion 63b of the cracking zone product stream 63 after compression to the first $H_2$ recovery unit 500 of the methanol loop. In such embodiment, a process for producing syngas and olefins as disclosed herein can advantageously comprise introducing at least a portion 52a of the residual as stream 52 from a portion of the purge stream from the first $H_2$ recovery unit 500 to the CPO reaction zone 100 via the CPO reactant mixture 10. In such embodiment, hydrocarbons in the cracking zone product stream 63 would accumulate less or would not accumulate in the methanol loop, thereby reducing the size of the methanol loop equipment. In such embodiment, hydrocarbons in the cracking zone product stream 63 can be advantageously converted to syngas in the CPO reaction zone 100. In such embodiment, the second $H_2$ recovery unit (e.g., second $H_2$ recovery unit 700) can be advantageously eliminated. Additional advantages of the processes for the production of syngas, olefins, and/or methanol as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

The yields from cracking light hydrocarbon feedstocks via a conventional cracking process (e.g., gas cracking process) are displayed in Table 1.

TABLE 1

Representative Yields from Light Hydrocarbon Feedstocks

| | Ethane (%) | Propane (%) | Butane (%) |
|---|---|---|---|
| Conversion per pass | 60 | 90 | 95 |
| Once through Yields (wt. %) | | | |
| $CO/CO_2/H_2S$ | 0.20 | 0.2 | 0.4 |
| $H_2$ | 3.5 | 1.5 | 1.0 |
| $CH_4$ | 4.3 | 23.8 | 22.5 |
| $C_2H_2$ | 0.2 | 0.7 | 0.5 |
| $C_2H_4$ | 47.7 | 36.5 | 34.5 |
| $C_2H_6$ | 40.0 | 3.2 | 4.5 |
| $C_3H_4$ | 0.05 | 0.5 | 0.4 |
| $C_3H_6$ | 1.15 | 14.7 | 16.5 |
| $C_3H_8$ | 0.4 | 10.0 | 0.4 |
| $C_4H_6$ | 1.4 | 2.65 | 3.5 |
| $C_4H_8$ | 0.15 | 1.15 | 3.2 |
| $C_4H_{10}$ | 0.25 | n.a | 3.4 |
| $C_{5+}$ | 0.7 | 5.1 | 9.2 |
| TOTAL | 100 | 100 | 100 |
| Ultimate Ethylene Yields Including Recycle Flows | 80 | 45.5 | 38.4 |

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention. Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing syngas and olefins comprising the following steps:
   (a) feeding a catalytic partial oxidation (CPO) reactant mixture to a CPO reaction zone; wherein the CPO reactant mixture comprises oxygen, first hydrocarbons, and optionally steam; wherein at least a portion of the CPO reactant mixture reacts, via an exothermic CPO reaction, in the CPO reaction zone to produce syngas; wherein the CPO reaction zone comprises a CPO catalyst; wherein the syngas comprises hydrogen (H2), carbon monoxide (CO), carbon dioxide (CO2), water, and unreacted first hydrocarbons, and wherein the syngas is characterized by an M ratio of the syngas, wherein the M ratio is a molar ratio defined as (H2−CO2)/(CO+CO2);
   (b) feeding a cracking zone feed to a cracking zone, wherein the cracking zone feed comprises second hydrocarbons; wherein at least a portion of the second hydrocarbons undergoes an endothermic cracking reaction in the cracking zone to produce a cracking zone product stream; wherein the first hydrocarbons and the second hydrocarbons are the same or different; wherein the cracking zone product stream comprises olefins, hydrogen, and unreacted second hydrocarbons; and (c) cooling the CPO reaction zone; wherein cooling the CPO reaction zone comprises heating the cracking zone while cooling the CPO reaction zone by heat transfer between the CPO reaction zone and the cracking zone, wherein the process further comprises the following steps: (1) separating at least a portion of the cracking zone product stream into a hydrogen stream and a hydrocarbons stream, wherein the hydrocarbons stream comprises olefins and unreacted hydrocarbons; (2) contacting at least a portion of the hydrogen stream with at least a portion of the syngas to produce a hydrogen-enriched syngas, wherein the hydrogen-enriched syngas is characterized by an M ratio greater than the M ratio of the syngas, and wherein the M ratio of the hydrogen-enriched syngas is equal to or greater than about 1.7.

2. The process of claim 1, wherein a common housing comprises both the CPO reaction zone and the cracking zone.

3. The process of claim 2, wherein the common housing further comprises a furnace zone; wherein a fuel stream is combusted in the furnace zone to provide for additional heat for the endothermic cracking reaction.

4. The process of claim 2, wherein the common housing further comprises a cracking reactor disposed therein, wherein the cracking reactor is characterized by a cracking reactor outer surface and by a cracking reactor inner surface, and wherein the cracking reactor inner surface defines the cracking zone.

5. The process of claim 4, wherein heating the cracking zone comprises heating the cracking zone feed within the cracking reactor disposed within the common housing.

6. The process of claim 4, wherein the cracking reactor comprises one or more tubes disposed within the common housing; wherein heating the cracking zone comprises heating the second hydrocarbons within the one or more tubes disposed within the common housing; wherein the CPO catalyst is disposed within the common housing; and wherein the CPO catalyst is located above the one or more tubes, below the one or more tubes, around the one or more tubes, on the one or more tubes, or combinations thereof.

7. The process of claim 4,
wherein the cracking reactor outer surface does not contact the CPO catalyst;
wherein the CPO reaction zone and the cracking zone are adjacent to each other, and wherein the CPO reaction zone and the cracking zone do not spatially overlap;
wherein at least a portion of the cracking reactor outer surface contacts the CPO catalyst;
wherein the common housing comprises a CPO catalyst bed disposed therein, wherein the CPO catalyst bed comprises the CPO catalyst, and wherein at least a portion of the cracking reactor is disposed within the CPO catalyst bed; and/or
wherein a layer of CPO catalyst coats at least a portion of the cracking reactor outer surface.

8. The process of claim 4, wherein the second hydrocarbons comprise ethane, propane, butane, naphtha, optionally methane, or combinations thereof; and wherein the olefins comprise ethylene.

9. The process of claim 1, wherein the CPO reaction zone is characterized by at least one CPO operational parameter selected from the group consisting of a CPO feed temperature of from about 25° C. to about 600° C.; a CPO effluent temperature of from about 300° C. to about 1,600° C.; a CPO pressure of from about 1 barg to about 90 barg; a CPO contact time of from about 0.001 milliseconds (ms) to about 5 seconds (s); a carbon to oxygen (C/O) molar ratio in the CPO reactant mixture of from about 0.5:1 to about 3:1, wherein the C/O molar ratio refers to the total moles of carbon (C) of hydrocarbons in the reactant mixture divided by the total moles of oxygen (O) in the reactant mixture; a steam to carbon (S/C) molar ratio in the CPO reactant mixture of from about 0.01:1 to less than about 2.4:1, wherein the S/C molar ratio refers to the total moles of water ($H_2O$) in the reactant mixture divided by the total moles of carbon (C) of hydrocarbons in the reactant mixture; and combinations thereof.

10. The process of claim 1, wherein the heat transfer between the CPO reaction zone and the cracking zone provides for near isothermal conditions in the CPO reaction zone, wherein the near-isothermal conditions comprise a temperature variation of less than about +100° C. across the CPO reaction zone and/or a catalyst bed thereof, and wherein the catalyst bed comprises the CPO catalyst.

11. The process of claim 1, wherein the first hydrocarbons and/or the second hydrocarbons comprise methane, ethane, propane, butanes, naphtha, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, or combinations thereof.

12. The process of claim 1, further comprising the following steps: (3) introducing at least a portion of the syngas and/or at least a portion of the hydrogen-enriched syngas to a methanol reactor to produce methanol; (4) optionally separating at least a portion of the hydrocarbons stream into an olefins stream and an unreacted hydrocarbons stream, wherein the olefins stream comprises at least a portion of the olefins in the hydrocarbons stream, and wherein the unreacted hydrocarbons stream comprises at least a portion of the unreacted hydrocarbons in the hydrocarbons stream; and (5) optionally recycling at least a portion of the hydrocarbons stream and/or at least a portion of the unreacted hydrocarbons stream to the cracking zone in step (b) and/or to the CPO reaction zone in step (a).

13. A process for producing methanol and ethylene comprising the following steps:
(a) feeding a catalytic partial oxidation (CPO) reactant mixture to a CPO reaction zone; wherein the CPO reactant mixture comprises oxygen, hydrocarbons, and optionally steam; wherein the CPO reaction zone comprises a CPO catalyst; wherein at least a portion of the CPO reactant mixture reacts under near-isothermal conditions, via an exothermic CPO reaction, in the CPO reaction zone to produce syngas; wherein the near-isothermal conditions comprise a temperature variation of less than about +100° C. across the CPO reaction zone and/or a catalyst bed thereof, and wherein the catalyst bed comprises the CPO catalyst; wherein the syngas comprises hydrogen (H2), carbon monoxide (CO), carbon dioxide (CO2), water, and unreacted hydrocarbons, and wherein the syngas is characterized by an M ratio of the syngas, wherein the M ratio is a molar ratio defined as (H2−CO2)/(CO+CO2);
(b) feeding a cracking zone feed to a cracking zone, wherein the cracking zone feed comprises ethane; wherein at least a portion of the ethane undergoes an endothermic cracking reaction in the cracking zone to produce a cracking zone product stream; wherein the cracking zone product stream comprises ethylene, hydrogen, and unreacted ethane;

(c) cooling the CPO reaction zone; wherein cooling the CPO reaction zone comprises heating the cracking zone while cooling the CPO reaction zone by heat transfer between the CPO reaction zone and the cracking zone; and wherein the heat transfer between the CPO reaction zone and the cracking zone provides for near-isothermal conditions in the CPO reaction zone;

(d) separating at least a portion of the cracking zone product stream in a separation unit into an ethylene stream, a hydrogen stream, and an unreacted ethane stream;

(e) contacting at least a portion of the hydrogen stream with at least a portion of the syngas to produce a hydrogen-enriched syngas, wherein the hydrogen-enriched syngas is characterized by an M ratio greater than the M ratio of the syngas, and wherein the M ratio of the hydrogen-enriched syngas is equal to or greater than about 1.7;

(f) optionally recycling at least a portion of the unreacted ethane stream to the cracking zone in step (b); and (g) introducing at least a portion of the syngas and/or at least a portion of the hydrogen-enriched syngas to a methanol reactor to produce methanol.

14. The process of claim 13, wherein a common housing comprises both the CPO reaction zone and the cracking zone; wherein the common housing further comprises a furnace zone; wherein a fuel stream is optionally combusted in the furnace zone to provide for additional heat for the endothermic cracking reaction; wherein the housing further comprises a cracking reactor disposed therein, wherein the cracking reactor is characterized by a cracking reactor outer surface and by a cracking reactor inner surface, and wherein the cracking reactor inner surface defines the cracking zone.

15. The process of claim 14, wherein the cracking reactor comprises one or more tubes disposed within the common housing; wherein heating the cracking zone comprises heating the ethane within the one or more tubes disposed within the common housing; wherein the CPO catalyst is disposed within the common housing; and wherein the CPO catalyst is located above the one or more tubes, below the one or more tubes, around the one or more tubes, on the one or more tubes, or combinations thereof.

16. The process of claim 13, wherein the separation unit comprises a pressure swing adsorption (PSA) unit, a membrane separation unit, a cryogenic separation unit, an oil scrubber separation unit, a size exclusion unit, or combinations thereof.

* * * * *